US010179118B2

(12) United States Patent
Karaborni et al.

(10) Patent No.: US 10,179,118 B2
(45) Date of Patent: Jan. 15, 2019

(54) PHARMACEUTICAL COMPOSITIONS OF DIMETHYL FUMARATE

(71) Applicant: XenoPort, Inc., Santa Clara, CA (US)

(72) Inventors: Sami Karaborni, Cupertino, CA (US); Wei Chen, Cupertino, CA (US); Suresh Kumar Manthati, Sunnyvale, CA (US)

(73) Assignee: ARBOR PHARMACEUTICALS, LLC, Atlanta, GA (US)

( * ) Notice: Subject to any disclaimer, the term of this patent is extended or adjusted under 35 U.S.C. 154(b) by 7 days.

(21) Appl. No.: 14/223,026

(22) Filed: Mar. 24, 2014

(65) Prior Publication Data

US 2014/0284245 A1    Sep. 25, 2014

Related U.S. Application Data

(60) Provisional application No. 61/805,869, filed on Mar. 27, 2013, provisional application No. 61/805,516, filed on Mar. 26, 2013, provisional application No. 61/805,137, filed on Mar. 25, 2013, provisional application No. 61/804,725, filed on Mar. 24, 2013.

(51) Int. Cl.

| A61K 31/336 | (2006.01) |
| A61K 31/194 | (2006.01) |
| A61J 1/03 | (2006.01) |
| A61K 31/225 | (2006.01) |
| A61K 31/215 | (2006.01) |
| A61K 31/343 | (2006.01) |
| A61K 31/381 | (2006.01) |
| A61K 31/403 | (2006.01) |
| A61K 9/48 | (2006.01) |

(52) U.S. Cl.
CPC .............. *A61K 31/336* (2013.01); *A61J 1/035* (2013.01); *A61K 31/194* (2013.01); *A61K 31/215* (2013.01); *A61K 31/225* (2013.01); *A61K 31/343* (2013.01); *A61K 31/381* (2013.01); *A61K 31/403* (2013.01); *A61K 9/4825* (2013.01)

(58) Field of Classification Search
CPC combination set(s) only.
See application file for complete search history.

(56) References Cited

U.S. PATENT DOCUMENTS

| 2,532,579 | A | * | 12/1950 | Thomas | A01N 37/42 |
| | | | | | 514/438 |
| 3,139,395 | A | * | 6/1964 | Griffin | C07C 255/45 |
| | | | | | 204/157.69 |
| 3,336,364 | A | | 8/1967 | Dill | |
| 3,751,277 | A | * | 8/1973 | Small | A61K 9/2826 |
| | | | | | 106/162.1 |
| 4,851,439 | A | | 7/1989 | Speiser et al. | |
| 4,863,916 | A | | 9/1989 | Habich et al. | |
| 4,959,389 | A | | 9/1990 | Speiser et al. | |
| 5,073,641 | A | | 12/1991 | Bundgaard et al. | |
| 5,145,684 | A | | 9/1992 | Liversidge et al. | |
| 5,149,695 | A | | 9/1992 | Speiser et al. | |
| 5,424,332 | A | | 6/1995 | Speiser et al. | |
| 5,451,667 | A | | 9/1995 | Speiser et al. | |
| 5,534,250 | A | | 7/1996 | Klaveness et al. | |
| 6,130,248 | A | | 10/2000 | Nudelman et al. | |
| 6,277,882 | B1 | | 8/2001 | Joshi et al. | |
| 6,355,676 | B1 | | 3/2002 | Joshi et al. | |
| 6,359,003 | B1 | | 3/2002 | Joshi et al. | |
| 6,379,697 | B1 | | 4/2002 | Gregoriadis et al. | |
| 6,436,992 | B1 | | 8/2002 | Joshi et al. | |
| 6,509,376 | B1 | | 1/2003 | Joshi et al. | |
| 6,613,800 | B1 | | 9/2003 | Smith | |
| 6,709,868 | B2 | | 3/2004 | Law et al. | |
| 6,723,508 | B2 | | 4/2004 | Sprenger et al. | |
| 6,858,750 | B2 | | 2/2005 | Joshi et al. | |
| 7,157,423 | B2 | | 1/2007 | Joshi et al. | |
| 7,320,999 | B2 | | 1/2008 | Joshi et al. | |
| 7,432,240 | B2 | | 10/2008 | Joshi et al. | |
| 7,612,110 | B2 | | 11/2009 | Joshi et al. | |
| 7,619,001 | B2 | | 11/2009 | Joshi et al. | |
| 7,638,118 | B2 | | 12/2009 | Flachsmann et al. | |
| 7,790,916 | B2 | | 9/2010 | Joshi et al. | |
| 7,803,840 | B2 | | 9/2010 | Joshi et al. | |
| 7,906,659 | B2 | | 3/2011 | Joshi et al. | |
| 7,915,310 | B2 | | 3/2011 | Joshi et al. | |
| 8,067,467 | B2 | | 11/2011 | Joshi et al. | |
| 8,148,414 | B2 | | 4/2012 | Gangakhedkar et al. | |
| 8,399,514 | B2 | | 3/2013 | Lukashev et al. | |
| 8,524,773 | B2 | | 9/2013 | Joshi et al. | |
| 8,669,281 | B1 | | 3/2014 | Zeidan et al. | |
| 8,759,393 | B2 | | 6/2014 | Joshi et al. | |
| 8,778,991 | B2 | | 7/2014 | Gangakhedkar et al. | |
| 8,785,443 | B2 | | 7/2014 | Gangakhedkar et al. | |
| 8,906,420 | B2 | | 12/2014 | Nilsson et al. | |
| 8,952,006 | B2 | | 2/2015 | Cundy et al. | |
| 2003/0018072 | A1 | | 1/2003 | Joshi et al. | |
| 2004/0054001 | A1 | | 3/2004 | Joshi et al. | |
| 2004/0102525 | A1 | | 5/2004 | Kozachuk | |
| 2005/0095292 | A1 | | 5/2005 | Benjamin et al. | |
| 2005/0096369 | A1 | | 5/2005 | Hoang | |
| 2005/0101779 | A1 | | 5/2005 | Sagi et al. | |
| 2005/0148664 | A1 | * | 7/2005 | Joshi | C07D 323/00 |
| | | | | | 514/529 |
| 2005/0208133 | A1 | | 9/2005 | Tsutsumi et al. | |

(Continued)

FOREIGN PATENT DOCUMENTS

| CN | 1616400 | 5/2005 |
| CN | 101318901 A | 12/2008 |

(Continued)

OTHER PUBLICATIONS

O'Donnell et al. "Remington The Science and Practice of Pharmacy" 21st Edition, 2005, Chapter 52, pp. 1025-1036.*

(Continued)

*Primary Examiner* — Andrew S Rosenthal
(74) *Attorney, Agent, or Firm* — King & Spalding

(57) ABSTRACT

Pharmaceutical compositions and dosage forms of dimethyl fumarate containing low levels of certain impurities are disclosed.

13 Claims, 3 Drawing Sheets

(56) References Cited

U.S. PATENT DOCUMENTS

| | | |
|---|---|---|
| 2006/0205659 A1 | 9/2006 | Joshi et al. |
| 2006/0269925 A1 | 11/2006 | Nunes et al. |
| 2007/0009475 A1 | 1/2007 | Flachsmann et al. |
| 2007/0027076 A1 | 2/2007 | Joshi et al. |
| 2007/0213300 A1 | 9/2007 | Liu et al. |
| 2007/0231382 A1 | 10/2007 | Karnachi et al. |
| 2007/0248663 A1 | 10/2007 | Joshi et al. |
| 2007/0253902 A1 | 11/2007 | Lobb et al. |
| 2008/0004344 A1 | 1/2008 | Nilsson et al. |
| 2008/0033199 A1 | 2/2008 | Lai et al. |
| 2008/0089861 A1 | 4/2008 | Went et al. |
| 2008/0089896 A1 | 4/2008 | Wang et al. |
| 2008/0227847 A1 | 9/2008 | Nilsson et al. |
| 2008/0233185 A1 | 9/2008 | Joshi et al. |
| 2008/0299196 A1 | 12/2008 | Nilsson et al. |
| 2008/0300217 A1 | 12/2008 | Nilsson |
| 2009/0011986 A1 | 1/2009 | Joshi et al. |
| 2009/0181085 A1 | 7/2009 | Joshi et al. |
| 2009/0182047 A1 | 7/2009 | Joshi et al. |
| 2009/0304790 A1 | 12/2009 | Nilsson et al. |
| 2010/0048651 A1 | 2/2010 | Gangakhedkar et al. |
| 2010/0099907 A1 | 4/2010 | Raillard et al. |
| 2010/0105784 A1 | 4/2010 | Remon et al. |
| 2010/0130607 A1 | 5/2010 | Gold |
| 2010/0144651 A1 | 6/2010 | Nilsson et al. |
| 2010/0226981 A1 | 9/2010 | Karaborni et al. |
| 2010/0247642 A1 | 9/2010 | Wu et al. |
| 2010/0260755 A1* | 10/2010 | Gammans ............ A61K 31/225 424/133.1 |
| 2011/0112196 A1 | 5/2011 | Lukashev |
| 2011/0124615 A1 | 5/2011 | Joshi et al. |
| 2011/0212169 A1 | 9/2011 | Bae et al. |
| 2011/0293711 A1 | 12/2011 | Joshi et al. |
| 2012/0034274 A1 | 2/2012 | Nilsson et al. |
| 2012/0034303 A1 | 2/2012 | Nilsson et al. |
| 2012/0095003 A1 | 4/2012 | Gangakhedkar et al. |
| 2012/0157523 A1 | 6/2012 | Gangakhedkar et al. |
| 2012/0165404 A1* | 6/2012 | Lukashev ................ A61K 9/00 514/547 |
| 2013/0065909 A1 | 3/2013 | Milne et al. |
| 2013/0172391 A1 | 7/2013 | Kahrs |
| 2013/0203753 A1 | 8/2013 | Cundy et al. |
| 2013/0259856 A1 | 10/2013 | Kaye |
| 2013/0259906 A1 | 10/2013 | Joshi et al. |
| 2013/0295169 A1 | 11/2013 | Goldman et al. |
| 2013/0302410 A1 | 11/2013 | Gold |
| 2013/0317103 A1 | 11/2013 | Lukashev |
| 2013/0324539 A1 | 12/2013 | Virsik et al. |
| 2014/0051705 A1 | 2/2014 | Cundy et al. |
| 2014/0056973 A1 | 2/2014 | Ma et al. |
| 2014/0056978 A1 | 2/2014 | Karaborni et al. |
| 2014/0057917 A1 | 2/2014 | Cundy et al. |
| 2014/0057918 A1 | 2/2014 | Wustrow et al. |
| 2014/0065211 A1 | 3/2014 | Karaborni et al. |
| 2014/0066505 A1 | 3/2014 | Joshi et al. |
| 2014/0099364 A2 | 4/2014 | Nilsson et al. |
| 2014/0163100 A1 | 6/2014 | Dawson et al. |
| 2014/0179778 A1 | 6/2014 | Mao et al. |
| 2014/0179779 A1 | 6/2014 | Chao |
| 2014/0193386 A1 | 7/2014 | Preiss-Bloom et al. |
| 2014/0193387 A1 | 7/2014 | Gruskin et al. |
| 2014/0193388 A1 | 7/2014 | Velders et al. |
| 2014/0193390 A1 | 7/2014 | Valenzano et al. |
| 2014/0193392 A1 | 7/2014 | Annunziata et al. |
| 2014/0193393 A1 | 7/2014 | Gulati |
| 2014/0193495 A1 | 7/2014 | Nilsson |
| 2014/0194427 A1 | 7/2014 | Chao |
| 2014/0200272 A1 | 7/2014 | Nilsson et al. |
| 2014/0200273 A1 | 7/2014 | Nilsson et al. |
| 2014/0200363 A1 | 7/2014 | Guzowski et al. |
| 2014/0205659 A1 | 7/2014 | Nilsson et al. |
| 2014/0275048 A1 | 9/2014 | Zeidan et al. |
| 2014/0275250 A1 | 9/2014 | Cundy et al. |
| 2014/0323570 A1 | 10/2014 | Gold |
| 2014/0329818 A1 | 11/2014 | Gangakhedkar et al. |
| 2014/0336151 A1 | 11/2014 | Chao |
| 2014/0364604 A1 | 12/2014 | Raillard et al. |
| 2014/0378542 A1 | 12/2014 | Mao et al. |
| 2015/0038499 A1 | 2/2015 | Virsik |
| 2015/0073049 A1 | 3/2015 | Mao et al. |
| 2015/0079180 A1 | 3/2015 | Karaborni et al. |
| 2015/0190360 A1 | 7/2015 | Cundy |
| 2015/0265707 A1 | 9/2015 | Manthati et al. |

FOREIGN PATENT DOCUMENTS

| | | | |
|---|---|---|---|
| CN | 101774913 A | 7/2010 | |
| DE | 1165586 | 3/1964 | |
| DE | 10360869 A1 | 4/2005 | |
| EP | 2692344 A1 | 2/2014 | |
| GB | 1153927 A | 6/1969 | |
| GB | 1404989 A | 9/1975 | |
| GB | 2285805 A | 7/1995 | |
| JP | S60181047 | 9/1985 | |
| JP | H03294245 | 12/1991 | |
| JP | 2001158760 | 6/2001 | |
| JP | 2002-027998 A | 1/2002 | |
| PL | 153592 | 10/1991 | |
| WO | WO 1996/036613 | 11/1996 | |
| WO | WO 1998/029114 | 7/1998 | |
| WO | 98/52549 | 11/1998 | |
| WO | WO 1998/053803 | 12/1998 | |
| WO | WO99/21559 | 5/1999 | |
| WO | 99/49858 | 10/1999 | |
| WO | WO 1999/051191 A1 | 10/1999 | |
| WO | WO 1999/062973 A1 | 12/1999 | |
| WO | WO 2000/010560 A1 | 3/2000 | |
| WO | WO 2000/012072 A2 | 3/2000 | |
| WO | 02/055063 A2 | 7/2002 | |
| WO | WO 2002/055066 | 7/2002 | |
| WO | WO 2002/055067 | 7/2002 | |
| WO | WO 2003/087174 | 10/2003 | |
| WO | 2005/023241 A1 | 3/2005 | |
| WO | 2005/027899 A1 | 3/2005 | |
| WO | WO-2005023241 A1 * | 3/2005 | ........... A61K 31/231 |
| WO | 2006/037342 A2 | 4/2006 | |
| WO | WO 2006/050730 | 5/2006 | |
| WO | WO 2006/122652 | 11/2006 | |
| WO | WO 2007/006307 | 1/2007 | |
| WO | WO 2007/006308 | 1/2007 | |
| WO | 2007/042034 A1 | 4/2007 | |
| WO | WO 2007/042035 | 4/2007 | |
| WO | WO 2008/096271 | 8/2008 | |
| WO | WO 2008/097596 | 8/2008 | |
| WO | WO 2010/022177 | 2/2010 | |
| WO | WO 2010/079221 | 7/2010 | |
| WO | WO 2010/079222 | 7/2010 | |
| WO | WO 2010/126605 | 11/2010 | |
| WO | WO 2011/080344 | 7/2011 | |
| WO | WO 2011/100589 | 8/2011 | |
| WO | WO 2012/162669 | 11/2012 | |
| WO | WO 2012/170923 | 12/2012 | |
| WO | WO 2013/022882 | 2/2013 | |
| WO | WO 2013/076216 | 5/2013 | |
| WO | WO 2013/119677 | 8/2013 | |
| WO | WO 2013/119791 | 8/2013 | |
| WO | WO 2014/020156 | 2/2014 | |
| WO | WO 2014/031894 | 2/2014 | |
| WO | WO 2014/031897 | 2/2014 | |
| WO | WO 2014/071371 | 5/2014 | |
| WO | WO 2014/096425 | 6/2014 | |
| WO | WO 2014/100728 | 6/2014 | |
| WO | WO 2014/190056 | 11/2014 | |
| WO | WO 2015/028472 | 3/2015 | |
| WO | WO 2015/028473 | 3/2015 | |

OTHER PUBLICATIONS

Pharmapedia (http://pharmapedia.wikidot.com/film-coating-materials-and-their-properties) accessed Aug. 8, 2017, pp. 1-25.*

O'Donnell et al. "Remington The Science and Practice of Pharmacy" 21st Edition, 2005, Chapter 52, pp. 1025-1036 (Year: 2005).*

(56) References Cited

OTHER PUBLICATIONS

McGinity, J.W. et al. "Aqueous Polymeric Coatings for Pharmaceutical Dosage Forms Third Edition" CRC Press, 2008. pp. 1-488 (Year: 2008).*
Augsburger, L.L. et al. "Pharmaceutical Dosage Forms—Tablets : Unit Operations and Mechanical Properties." Chapter 15. Baton Rouge: CRC Press, 2008. pp. 485-517 (Year: 2008).*
Griffin, G.W. et al. "The Chemistry of Photodimers of Maleic and Fumaric Acid Derivatives. I. Dimethyl Fumarate Dimer" J. Am. Chem. Soc., 1961, 83 (12), pp. 2725-2728 (Year: 1961).*
Altmeyer et al., Antipsoriatic effect of fumaric acid derivatives, J. Amer. Acad. Derm. (1994), 30(6): 977-981.
Altschul et al., "Gapped BLAST and PSI-BLAST: a new generation of protein database search programs," Nucleic Acids Research, 1997, vol. 25, No. 17, pp. 3389-3402.
Ashe, Learning and memory in transgenic mice modeling Alzheimer's disease. Learning & Memory (2001), 8, 301-308.
Associated Press; FDA mulls drug to slow late-stage Alzheimer's [online]; [retrieved on Sep. 24, 2003]; retrieved from the internet, <http://www.cnn.com/2003/HEALTH/conditions/09/24/alzheimers.drug.ap/index.html>; Sep. 24, 2003; 2 pages.
Atreya et al., "NF-κB in inflammatory bowel disease," Journal of Internal Medicine (2008), 263(6), pp. 591-596.
Author Unknown, BG 00012, BG 12/oral fumarate, FAG-201, second-generation fumarate derivative—Fumapharm/Biogen Idec, Drugs RD (2005), 6(4): 229-230.
Bar-Or et al., "Clinical efficacy of BG-12 (dimethyl fumarate) in patients with relapsing-remitting multiple sclerosis: subgroup analyses of the Define study," J. Neurol, 2013, vol. 260, pp. 2297-2305.
Bardgett et al., NMDA receptor blockade and hippocampal neuronal loss impair fear conditioning and position habit reversal in C57B1/6 mice. Brain Res Bull (2003), 60, 131-142.
Barnes, "Mediators of chronic obstructive pulmonary disease," Pharmacological Reviews (2004), 56(4), pp. 515-548.
Behari et al., Baseline characteristics of a subpopulation of Indian patients enrolled in two phase 3 trials for oral BG-12 in relapsing-remitting multiple sclerosis, 62nd Ann Mtg. Amer. Acad. Neurol. (2010), poster, 2 pages.
Benoit et al., Etude Clinique de L'ester B-Morpholinoethylique de L'Acide Niflumique en Stomatologie Infantile, Rev. Odontostomatol Midi Fr. (1975), 4: 249-261.
Bertone, "Prevalence of Gastric Ulcers in Elite, Heavy Use Western Performance Horses," AAEP Proceedings (2000). 46: 256-259.
Bhagavathula et al., 7-Chloro-5-(4-hydroxyphenyl)-1-methyl-3-(naphthalen-2-ylmethyl)-4,5-dihydro-1H-benzo[b][1,4]diazepin-2(3H)-one (Bz-423), a benzodiazepine, suppresses keratinocyte proliferation and has antipsoriatic activity in the human skin-severe, combined immunodeficient mouse transplant model. J Pharmacol Expt'l Therapeutics (2008), 324(3), 938-947.
Blad, et al., "Biological and Pharmacological Roles of HCA Receptors", Advances in Pharmacology, 2011, 62: 219-250.
Blandini, et al., "Glutamate and Parkinson's disease," Molecular Neurobiology (1996), 12(1), pp. 73-94.
Boehncke, "Animal Models of T Cell-Mediated Skin Diseases, Chapter 12: The Psoriasis SCID Mouse Model: A Tool for Drug Discovery?" Ernst Schering Res Found Workshop 50, Zollner et al., eds. New York: Springer (2005) pp. 213-234.
Brewer, et al., "Fumaric acid esters in the management of severe psoriasis", Clinical Experimental Dermatology, 2007, 32: 246-249.
Brown et al., "Goodman & Gilman's The Pharmacological Basis of Therapeutics, Tenth Edition: Chapter 7, Muscarinic Receptor Agonists and Antagonists," A. Gilman, J. Hardman and L. Limbird, eds., Mc-Graw Hill Press, 2001, pp. 155-173.
Bruhn et al., "Concordance between enzyme activity and genotype of glutathione S-transferase theta (GSTT1)," Biochemical Pharmacology, 1998, vol. 56, pp. 1189-1193.
Bundgaard et al., Esters of N,N-Disubstituted 2-Hydroxyacetamides as a Novel Highly Biolabile Prodrug Type for Carboxylic Acid Agents, J. Med. Chem. (1987), 30(3): 451-454.
Bundgaard et al., Glycolamide esters as a novel biolabile prodrug type for non-steroidal anti-inflammatory carboxylic acid drugs, Int. J. Pharm. (1988) 43: 101-110.
Büyükcoskun, Central Effects of Glucagon-like Peptide-1 on Cold Restraint Stress-induced Gastric Mucosal Lesions, Turk J. Gastroenterol (2007), 18(3): 150-156.
Büyükcoskun, Role of Intracerebroventricular Vasopressin in the Development of Stress-Induced Gastric Lesions in Rats, Physiol. Res. (1999), 48: 451-455.
Caira, "Crystalline Polymorphism of Organic Compounds," Topics in Current Chemistry, Springer, Berlin, DE (1998), vol. 198, pp. 163-208.
Camandola et al., "NF-κB as a therapeutic target in neurodegenerative diseases," Expert Opinion Therapeutic Targets (2007), 11(2), pp. 123-132.
Capello, et al., "Marburg type and Balo's concentric sclerosis: Rare and acute variants of multiple sclerosis", Neurological Sciences 200411 IT, vol. 25, No. Suppl. 4, Nov. 2004, pp. S361-S363.
Cavarra et al., Effects of cigarette smoke in mice with different levels of α1-proteinase inhibitor and sensitivity to oxidants. Am J Respir Crit Care Med (2001), 164, 886-890.
Champion, et al., "Flushing and Flushing Syndromes, Rosacea and Perioral Dermatitis", Rook Wilkinson Ebling Textbook of Dermatology, 6th ed. vol. 3, Oxford, UK: Blackwell Scientific, 1998, pp. 2099-2104.
Chaudhary et al., "Enhancement of solubilization and bioavailability of poorly soluble drugs by physical and chemical modifications: A recent review," Journal of Advanced Pharmacy Education & Research (2012), 2(1), pp. 32-67.
Chen et al., "Nanonization strategies for poorly water-soluble drugs," Drug Discovery Today, 2010, pp. 1-7.
Cockcroft et al., Bronchial reactivity to inhaled histamine: a method and clinical survey. Clin Allergy (1977), 7, 235-243.
Cross, et al. Dimethyl Fumarate, an Immune Modulator and Inducer of the Antioxidant Response, Suppresses HIV Replication and Macrophage-Mediated Neurotoxicity: A Novel Candidate for HIV Neuroprotection. The Journal of Immunology, (2011), 187(10): 5015-5025.
D'Acquisto et al., Inhibition of nuclear factor kappa B (NF-κB): an emerging theme in anti-inflammatory therapies. Molecular Interventions (2002), 2(1), 22-35.
Damasio; "Alzheimer's Disease and Related Dementias;" Cecil Textbook of Medicine; 1996; 20th Edition, vol. 2; pp. 1992-1996.
De Jong et al., Selective stimulation of T helper 2 cytokine responses by the anti-psoriasis agent monomethylfunarate, Eur. J. Immunol. (1996), 26: 2067-2074.
Dibbert, et al.,: "Detection of fumarate-glutathione adducts in the portal vein blood of rats: Evidence for rapid dimethyl fumarate metabolism", Archives of Dermatological Research 2013 Springer Verlag Deu, vol. 305, No. 5, Jul. 2013 (Jul. 2013), pp. 447-451.
Eberle, et al. Fumaric Acid Esters in Severe Ulcerative Necrobiosis Lipoidica: A Case Report and Evaluation of Current Therapies. Acta Dermato-Venereologica (2010) 90(1): 104-106.
Ellrichmann et al., Efficacy of fumaric acid esters in the R6/2 and YAC128 models of Huntington's disease, PLOS One (2011), 6(1): 11 pages.
Etter et al., "The Use of Cocrystallization as a Method of studying Hydrogen Bond Preferences of 2-Aminopyrimidine," Journal of the Chemical Society (1990), No. 8, pp. 589-591.
Etter et al., "Graph Set Analysis of Hydrbgen-Bond Patterns in Organic Crystals," Acta Crystallogr., Sect. B, Struct. Sci. (1990), B46, pp. 256-262.
Etter et al., "Hydrogen Bond Directed Cocrystallization and Molecular Recognition Properties of Diarylureas," Journal of the Chemical Society (1990), No. 112, pp. 8415-8426.
Eugster et al., Superantigen overcomes resistance of IL-6 deficient mice towards MOG-induced EAE by a TNFR1 controlled pathway. Eur J Immunol (2001), 31, 2302-2312.
European Commission Health & Consumer Protection Directorate-General, Report of the scientific committee on animal nutrition on the safety of fumaric acid, adopted Jan. 22, 2003: 18 pages.

(56) References Cited

OTHER PUBLICATIONS

Feinstein et al., Anti-inflammatory and prometabolic effects of BG-12 in glial cells, 26th Congress Eur. Cmtee. Treat. Res. Mult. Scler. (2010), poster: 1 page.
Fits et al., Imiquimod-Induced Psoriasis-Like Skin Inflammation in Mice Is Mediated via the IL-23/IL-17 Axis, J. Immunol. (2009), 182: 5836-5845.
Fox et al., Baseline characteristics of patients in a randomized, multicenter, placebo-controlled and active comparator trial evaluating efficacy and safety of BG-12 in relapsing-remitting multiple sclerosis: the Confirm trial, 62nd Ann Mtg. Amer. Acad. Neurol. (2010), poster, 2 pages.
Fox et al., Placebo-controlled phase 3 study of oral BG-12 or glatiramer in multiple sclerosis, N Engl J Med. Sep. 20, 2012;367(12):1087-97. Erratum in: N Engl J Med. Oct. 25, 2012;367(17):1673.
Frycak et al., Evidence of covalent interaction of fumaric acid esters with sulfhydryl groups in peptides, J. Mass. Spectrom. (2005), 40: 1309-1318.
Gadad et al., Synthesis, spectral studies and anti-inflammatory activity of glycolamide esters of niflumic acid as potential prodrugs, Arzneim Forsch Drug Res. (2002), 52(11): 817-821.
Gambichler, et al. Clearance of Necrobiosis lipoidica with Fumaric Acid Esters. Dermatology (2003), 207(4): 422-424.
Gesser et al., Dimethylfumarate specifically inhibits the mitogen and stress-activated kinases 1 and 2 (MSK1/2): Possible role for its anti-psoriatic effect. J Investigative Dermatology (2007), 127, 2129-2137.
Goke et al., Effect of a Specific Serine Protease Inhibitor on the Rat Pancreas: Systemic Administration of Camostate and Exocrine Pancreatic Secretion, Digestion (1984) 30: 171-178.
Gogas et al., Comparison of the efficacy and tolerability of a novel methyl hydrogen fumarate prodrug with dimethyl fumarate in rodent EAE and GI irritation models, XenoPort, Inc.; 26th Congress of the European Committee for Treatment and Research in Multiple Sclerosis (ECTRIMS), 2010 (Poster #671), 1 page.
Gold et al., Baseline characteristics of patients in the Define trial: a randomized, multicenter, double blind, placebo-controlled, phase 3 study of BG-12 in relapsing-remitting multiple sclerosis, 62nd Ann Mtg. Amer. Acad. Neurol. (2010), poster, 2 pages.
Gold et al., Placebo-controlled phase 3 study of oral BG-12 for relapsing multiple sclerosis, N Engl J Med. Sep. 20, 2012;367(12):1098-107, Erratum in: N Engl J Med. Dec. 13, 2012;367(24):2362.
Gorbitz et al., "On the inclusion of solvent molecules in the crystal structures of organic compounds," Acta Cryst. (2000), B56, pp. 526-534.
Ghoreschi Kamran, et al., "Furmarates improve psoriasis and multiple sclerosis by inducing type II dendritic cells", The Journal of Experimental Medicine, Rockefeller University Press, US, vol. 208, No. 11, Oct. 24, 2011 (Oct. 24, 2011), pp. 2291-2303.
Grigorian et al., Control of T-cell mediated autoimmunity by metabolite flux to N-glycan biosynthesis, J. Bio. Chem. (2007), 282(27): 20027-20035.
Guenther, et al., Macular Exanthema Due to Fumaric Acid Esters. Annals of Pharmacotherapy (2003), 37(2): 234-236.
Gurney et al., Motor neuron degeneration in mice that express a human Cu,Zn superoxide dismutase mutation. Science (1994), 264, 1772-1775.
Hanson et al., Nicotinic acid- and monomethyl funarate-induced flushing involves GPR109A expressed by keratinocytes and COX-2-dependent prostanoid formation in mice, J. Clin. Invest. (2010), 120(8): 2910-2919.
Heiligenhaus, et al. Influence of dimethylfumarate on experimental HSV-1 necrotizing keratitis. Graefe's Archive for Clinical and Experimental Ophthalmology (2004), 242(10): 870-877.
Heiligenhaus, et al. Improvement of herpetic stromal keratitis with fumaric acid derivate is associated with systemic induction of T helper 2 cytokines. Clinical and Experimental Immunology (2011), 142(1): 180-187.

Hiraku et al., Absorption and Excretion of Camostat Orally Administered to Male Rabbit and Healthy Subject, Iyakuhin Kenkyu (1982) 13(3): 756-765.
Hoefnagel, et al., "Long-term safety aspects of systemic therapy with fumaric acid esters in severe psoriasis", British Journal of Dermatology, 2003, 149: 363-369.
Horig et al., From bench to clinic and back: Perspective on the 1st IQPC Translational Research Conference, J. Transl. Med. (2004), 2(44), 8 pages.
Hoxtermann et al., Fumaric acid esters suppress peripheral CD4- and CD8-positive lymphocytes in psoriasis, Dermatology (1998), 196: 223-230.
Hurd et al., Vinylation and the Formation of Acylals:, J. Am. Chem. Soc.; vol. 78; Jan. 5, 1956; pp. 104-106.
Iyer et al., Synthesis of iodoalkylacylates and their use in the preparation of S-alkyl phosphorothiolates. Synth Commun (1995), 25(18), 2739-2749.
Jennings, Squamous cell carcinoma as a complication of fumaric acid ester immunosuppression, J. Eur. Acad. Dermatol. Venereol. (2009), DOI: 10.1111/j.1468-3083.2009.03234.x, 1 page.
Jurjus et al., Animal models of inflammatory bowel disease. J Pharmacol Toxicol Methods (2004), 50, 81-92.
Kappos et al., Efficacy and safety of oral fumarate in patients relapsing-remitting multiple sclerosis: a multicentre, randomised, double-blind, placebo controlled phase IIb study, Lancet (2008), 372: 1463-1472.
Kamimura et al., "Stereoselective formation of optically active 2-oxy-1,3-oxazolidin-4-ones from chiral O-acylmandelamides or lactamides", Tetrahedron 58, 2002, 8763-8770.
Khan et al., Synthesis and biological evaluation of glycolamide esters as potential prodrugs of some non-steroidal anti-inflammatory drugs, Ind. J. Chem. (2002) 41B: 2172-2175.
Klein, et al. Off-label use of fumarate therapy for granulomatous and inflammatory skin diseases other than psoriasis vulgaris: a retrospective study. (2012), Journal of the European Academy of Dermatology and venereology (2012), 26(11): 1400-1406 (also on-line ref: Klein, et al., (2011), J Eur Acad Dermatol Venereol doi: 10.1111/j.1468-3083.2011.04303.x).
Kreuter et al., Fumaric acid esters in necrobiosis lipoidica: results of a prospective noncontrolled study. British Journal of Dermatology (2005) 153(4): 802-807.
Kumar et al., "Molecular Complexes of Some Mono- and Dicarboxylic Acids with trans-1,4-Dithiane-1,4-dioxide," American Chemical Society, Crystal Growth & Design (2002), 2(4), pp. 313-318.
Layzer; "Section Five—Degenerative Diseases of the Nervous System"; Cecil Textbook of Medicine; 1996; 20th Edition, vol. 2; pp. 2050-2057.
Lee et al., Spotlight on fumarates, Int. MS J. (2008), 15: 12-18.
Lehmann et al., Dimethylfumarate induces immunosuppression via glutathione depletion and subsequent induction of heme oxygenase 1. J Investigative Dermatology (2007), 127, 835-845.
Lei et al., "Novel Technology of Dimethyl Fumarate Synthesis," Ziyuan Kaifa Yu Shichang (2011), 27(9), pp. 787-789.
Linker et al., Identification and development of new therapeutics for multiple sclerosis, Treds. Pharm. Sci. (2008), DOI 10.1016/j.tips.2008.07.012, 8 pages.
Linker et al., Fumaric acid esters exert neuroprotective effects in neuroinflammation via activation of the Nrf2 antioxidant pathway, Brain (2011), 134: 678-692.
Litjens e al., Monomethylfumarate affects polarization of monocyte-derived dendritic cells resulting in down-regulated Th1 lymphocyte responses, Eur. J. Immunol. (2004), 34: 565-575.
Litjens et al., Pharmacokinetics of oral fumarates in healthy subjects, Br. J. Clin. Pharmacol. (2004), 58(4): 429-432.
Litjens et al., Effects of monomethylfumarate on dendritic cell differentiation, Br. J. Dermatol. (2006), 154: 211-217.
Loewe et al., "Dimethylfumarate inhibits TNF-induced nuclear entry of NF-κB/p65 in human endothelial cells," The Journal of Immunology (2002), 168, pp. 4781-4787.
Loewe et al., Dimethylfumarate impairs melanoma growth in metastasis, Cancer Res. (2006), 66(24): 11888-11896.

(56) References Cited

OTHER PUBLICATIONS

Lopez-Diego et al., Novel therapeutic strategies for multiple sclerosis—a multifaceted adversary, Nat. Review. Drug Disc. (2008), 7:909-925.
Los et al., Nuevos Estered De Acidos Anilinonicotinicos Y N-Fenilantranilicos Sustituidos, II Farmaco—Ed. Sc. (1980), 36(5): 372-85.
Lukashev et al., Activation of Nrf2 and modulation of disease by BG00012 (dimethyl fumarate) suggest a dual cytoprotective and anti-inflammatory mechanism of action, 62nd Ann Mtg. Amer. Acad. Neurol. (2010), poster, 4 pages.
Mandhane, et al., Adenosine A2 receptors modulate haloperidol-induced catalepsy in rats. Eur. J. Pharmacol (1997), 328, 135-141.
Martin, "Molecular basis of the neurodegenerative disorders," The New England Journal of Medicine (1999), 340(25), pp. 1970-1980.
Martorana et al., Roflumilast fully prevents emphysema in mice chronically exposed to cigarette smoke. Am J Respir Crit Care Med (2005), 172, 848-853.
Meissner et al., "Dimethyl fumarate—only an anti-psoriatic medication?", Journal Der Deutschen Demrmatologischen Gesellschaft (2012), vol. 10, pp. 793-801.
Menter et al., Guidelines of care for the management of psoriasis and psoriatic arthritis, J. Am. Acad. Dermatol. (2009), doi:10.1016/j.jaad.2009.03.027, 35 pages.
Merisko-Liversidge et al., "Nanosizing: a formulation approach for poorly-water-soluble compounds," European Journal of Pharmaceutical Sciences, 18 (2003), pp. 113-120.
Miller et al., Experimental Autoimmune Encephalomyelitis in the Mouse, Current Protocols in Immunology (2007), Supp. 78: 15.1.1-15.1.18.
Milo, et al., "Combination therapy in multiple sclerosis", Journal of Neuroimmunology, vol. 231, No. 1, 2011, pp. 23-31.
Mosmann et al., TH1 and TH2 cells: different patterns of lymphokine secretion lead to different functional properties, Ann. Rev. Immunol. (1989), 7: 145-73.
Mrowietz, et al., "Treatment of Psoriasis with Fumaric Acid Esters: Results of a prospective Multicenter Study," British Journal of Dermatology (1998), 138: 456-460.
Mrowietz et al., "Treatment of severe psoriasis with fumaric acid esters: scientific background and guidelines for therapeutic use," British Journal of Dermatology (1999), 141, pp. 424-429.
Mrowietz et al., Treatment of psoriasis with fumaric acid esters (Fumaderm®), JDDG (2007), DOI: 10.1111/j.1610-0387.2007.06346.x, 2 pages.
Muller et al., "High-performance liquid chromatography/fluorescence detection of S-methylglutathione formed by glutathione-S-transferase T1 in vitro," Arch Toxicol, 2001, vol. 74, pp. 760-767.
Murakami et al., Suppression of a dextran sodium sulfate-induced colitis in mice by zerumbone, a subtropical ginger sesquiterpene, and nimesulide: separately and in combination. Biochemical Pharmacol (2003), 66, 1253-1261.
Naldi et al., Psoriasis (chronic plaque), Clin. Evid. (2009), 1(1706): 50 pages.
Nelson, et al., Effect of Dietary Inducer Dimethylfumarate on Glutathione in Cultured Human Retinal Pigment Epithelial Cells. Investigative Ophthalmology and Visual Science (1999), 40(9): 1927-1935.
Neymotin et al., Neuroprotective effect of Nrf2/AFE activators, CDDO ethylamide and CDDO trifluoroethylamide, in a mouse model of amyotrophic lateral sclerosis, Free Rad. Bio. Med (2011), 51: 88-96.
Nibbering et al., Intracellular signalling by binding sites for the antipsoriatic agent monomethylfumarate on human granulocytes, Br. J. Dermatol. (1997), 137: 65-75.
Nielsen, et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, Apr. 1988, pp. 285-298.
Offermans, The nicotinic acid receptor GPR109A (HM74A or PUMA-G) as a new therapeutic agent, Trends Pharm. Sci. (2006), 27(7): 384-390.
O'Toole, et al., Treatment of Carcinoid Syndrome: A Prospective Crossover Evaluation of Lanreotide versus Octreotide in Terms of Efficacy, Patient Acceptability, and Tolerance, American Cancer Society, Feb. 15, 2000, 88(4), 770-776.
Panagiotou et al., "Form Nanoparticles via Controlled Crystallization," Chemical Engineering Progress; Oct. 2008, 104, 10, pp. 33-39.
Pathak et al., "Supercritical fluid technology for enhanced drug delivery," Expert Opin. Drug Deliv. (2005) 2(4):747-761.
Peeters et al., Fumaric acid therapy for psoriatic arthritis. A randomized, double-blind, placebo-controlled study, Br. J. Rheumatol. (1992), 31(7): 502-504.
Pemble et al., "Human glutathione S-transferase Theta (GSTT1): cDNA cloning and the characterization of a genetic polymorphism," Biochem. J., 1994, vol. 300, pp. 271-276.
Rantanen, The cause of the Chinese sofa/chair dermatitis epidemic is likely to be contact allergy to dimethylfumarate, a novel potent contact sensitizer, Br. J. Dermatol. (2008), 159: 218-221.
Reddingius, Bioanalysis and pharmacokinetics of fumarates in humans, Ph.D. dissertation ETH No. 12199, Swiss Fed. Inst. Tech. Zurich (1997), 82 pages.
Reich et al., Efficacy and safety of fumaric acid esters in the long-term treatment of psoriasis—a retrospective study (Future), JDDG (2009), DOI: 10.1111/j.1610-0387.2009.07120.x, 8 pages.
Richman et al., Nicotinic acid receptor agonists differentially activate downstream effectors, J. Bio. Chem. (2007), 282(25): 18028-18036.
Roll et al., Use of fumaric acid esters in psoriasis, Indian J. Dermatol. Ven. Lep. (2007), 73: 133-137.
Rostami-Yazdi, et al., "Detection of Metabolites of Fumaric Acid Esters in Human Urine: Implications for their mode of action", Journal of Investigative Dermatology, 2008, pp. 1-3.
Rostami-Yazdi et al., Pharmacokinetics of antipsoriatic fumaric acid esters in psoriasis patients, Arch. Dermatol. Res. (2010), 302: 531-538.
Rowland et al., "Amyotrophic lateral sclerosis," The New England Journal of Medicine (2001), 344(22), pp. 1688-1700.
Rubant et al., Dimethylfumarate reduces leukocyte rolling in vivo through modulation of adhesion molecule expression, J. Invest. Dermatol. (2007), 128: 326-331.
Sawant et al., "Necessity of Establishing Chemical Integrity of Polymorphs of Drug Substance Using a Combination of NMR, HPLC, Elemental Analysis, and Solid-State Characterization Techniques: Case Studies," Organic Process Research & Development (2013), vol. 17, No. 3, pp. 519-532.
Schafer et al., "Failure is an option: learning from unsuccessful proof-of-concept trials", Drug Discovery Today, vol. 13, Nos. 21/22; Nov. 2008; pp. 913-916.
Schmidt, et al., "Reactivity of dimethyl fumarate and methylhydrogen fumarate towards glutathione and N-acetyl-1-cysteine-Preparation of S-substituted thiosuccinic acid esters", Bioorganic & Medicinal Chemistry, Pergamon, GB, vol. 15, No. 1 Nov. 15, 2006 (Nov. 15, 2006), pp. 333-342.
Seder et al., Acquisition of lymphokine-producing phenotype by CD4+ T-cells, Ann. Rev. Immunol. (1994), 12: 635-73.
Shan et al., "The role of cocrystals in pharmaceutical science," Drug Discovery Today (2008), 13(9/10), pp. 440-446.
Sharma et al., Distal effect on mass spectral fragmentations of glycolamide esters of 6-methoxy-2-naphthylacetic acid (6-MNA) and the crystal structure of N,N'-dimethyl-glycolamide ester of 6-MNA, Ind. J. Chem. (2004) 43B: 1758-1764.
Soelberg Sorensen et al., Oral fumarate for relapsing-remitting multiple sclerosis, Lancet (2008), 372: 1447-1448.
Spencer et al., Induction of glutathione transferases and NAD(P)H: quinone reductase by fumaric acid derivatives in rodent cells and tissues, Cancer Res. (1990), 50: 7871-7875.
Spencer, "Tecfidera: an approach for repurposing," Pharmaceutical Patent Analyst, 2014, vol. 3(2), pp. 183-198.

(56) References Cited

OTHER PUBLICATIONS

Sprenger et al., "Characterization of the glutathione S-transferase GSTT1 deletion: discrimination of all genotypes by polymerase chain reaction indicates a trimodular genotype-phenotype correlation," Pharmacogenetics, 2000, vol. 10, pp. 557-565.

Stoof et al., The antipsoriatic drug dimethylfumarate strongly suppresses chemokine production in human keratinocytes and peripheral blood mononuclear cells, Br. J. Dermatol. (2001), 144: 1114-1120.

Tabruyn et al., NF-κB: a new player in angiostatic therapy. Angiogenesis (2008), 11, 101-106.

Talath et al., Stability studies of some glycolamide ester prodrugs of niflumic acid in aqueous buffers and human plasma by HPLC with UV detection, Arz. Forsch Drug Res. (2006), 56(9): 631-639.

Talath et al., Synthesis, stability studies, anti-inflammatory activity and ulcerogenicity of morpholinoalkyl ester prodrugs of niflumic acid, Arz. Forsch Drug Res. (2006), 56(11): 744-752.

Tang et al., The psoriasis drug monomethylfumarate is a potent nicotinic acid receptor agonist, Biochem. Biophys. Res. Comm. (2008), doi:10.1016/j.bbrc.2008.08.041, 4 pages.

Thing et al., "Prolonged naproxen joint residence time after intra-articular injection of lipophilic solutions comprising a naproxen glycolamide ester prodrug in the rat", International Journal of Pharmaceutics 451; Apr. 2013; pp. 34-40.

Thomson et al., FK 506: a novel immunosuppressant for treatment of autoimmune disease: rationale and preliminary clinical experience at the University of Pittsburgh, Springer Semin. Immunopathol. (1993), 14(4): 323-344.

Tracey et al., "Tumor necrosis factor antagonist mechanisms of action: a comprehensive review," Pharmacology & Therapeutics (2008), 117, pp. 244-279.

Treumer et al., Dimethylfumarate is a potent inducer of apoptosis in human T cells. J Invest Dermatol (2003), 121, 1383-1388.

Van Schoor et al., Effect of inhaled fluticasone on bronchial responsiveness to neurokinin A in asthma. Eur Respir J (2002), 19, 997-1002.

Van Schoor et al., The effect of the NK2 tachykinin receptor antagonist SR 48968 (saredutant) on neurokinin A-induced bronchoconstriction in asthmatics, Eur Respir J (1998) 12: 17-23.

Vandermeeren et al., Dimethylfumarate is an inhibitor of cytokine-induced E-selectin, VCAM-1, and ICAM-1 expression in human endothelial cells. Biochem Biophys Res Commun (1997), 234, 19-23.

Villegas et al., A new flavonoid derivative, dosmalfate, attenuates the development of dextran sulphate sodium-induced colitis in mice. Int'l Immunopharmacol (2003), 3, 1731-1741.

Virley, "Developing therapeutics for the treatment of multiple sclerosis," NeuroRx: The Journal of the American Society for Experimental NeuroTherapeutics (2005), vol. 2, pp. 638-649.

Vishweshwar et al., "Pharmaceutical Co-Crystals," Journal of Pharmaceutical Sciences (2006), 95(3), pp. 499-516.

Wadhwa et al., Glycolamide esters of 6-methoxy-2-naphthylacetic acid as potential prodrugs—Synthetic and spectral studies, Ind. J. Chem. (1995), 34B: 408-415.

Wain et al., Treatment of severe, recalcitrant, chronic plaque psoriasis with fumaric acid esters: a prospective study, Br. J. Dermatol. (2009), DOI 10.1111/j.1365-2133.2009.09267.x, 8 pages.

Wakkee et al., "Drug evaluation: BG-12, an immunomodulary dimethylfumarate," Current Opinion in Investigational Drugs (2007), 8(11), pp. 955-962.

Wang, et al., Evidence-Based Treatment of Chronic Leg Ulcers in A Patient with Necrobiosis Lipoidica Deabeticorum. Chinese Journal of Evidence-Based Medicine (2007), 7(11): 830-835.

Weber et al., Synthesis, In Vitro Skin Permeation Studies, and PLS-Analysis of New Naproxen Derivatives, Pharm. Res. (2001) 18(5): 600-607.

Weber et al., Treatment of disseminated granuloma annulare with low-dose fumaric acid, Acta Derm. Venereol. (2009), 89: 295-298.

Werdenberg et al., Presystemic metabolism and intestinal absorption of antipsoriatic fumaric acid esters, Biopharm. Drug. Dispos. (2003), 24: 259-273.

Whiteley et al., Models of Inflammation: Measuring Gastrointestinal Ulceration in the Rat, Curr. Protocol. Pharm. (1998): 10.2.1-10.2.4.

Wingerchuk et al., "Multiple sclerosis: current pathophysiological concepts," Laboratory Investigation (2001), 81(3), pp. 263-281.

Winkler, et al., Oxidative damage and age-related macular degeneration. Molecular vision, (1999), 5:32, 11 pages.

Woodworth et al., Oral BG-12 in combination with interferon beta or glatiramer acetate: pharmacokinetics, safety and tolerability, 26th Congress Eur. Cmtee. Treat. Res. Mult. Scler. (2010), poster: 1 page.

Wu et al., "Regulatory perspectives of Type II prodrug development and time-dependent toxicity management: Nonclinical Pharm/Tox analysis and the role of comparative toxicology", Science Direct, Toxicology 236; Apr. 2007; pp. 1-6.

Wustrow et al., Comparison of the efficacy and tolerability of a novel methyl hydrogenfumarate prodrug with dimethylfumarate in rodent EAE and GI irritation models, XenoPort, Inc., Oct. 13-16, 2010, 1 page.

Xenoport, Inc., XenoPort announces presentation of preclinical data for novel fumarate analog XP23829 at ECTRIMS, Press Release dated Oct. 13, 2010, 3 pages.

Yamada et al., "Synthesis and Polymerization of Unsaturated Dibasic Acid Derivatives," Yuki Gosei Kagaku Kyokaishi (1965), 23(2), 19 pages.

Yang et al., Neuroprotective effects of the triterpenoid, CDDO methyl amide, a potent inducer of Nrf2-mediated transcription, PLOS One (2009), 4(6) doi:10.1371/journal.pone.0005757: 13 pages.

Zhang et al., "Synthesis of Dimethyl Fumarate with Orthogonal Test," Jingxi Huagong Zhongjianti (2006), 36(6), pp. 71-72.

Zhao et al., "Synthesis and antimicrobial active of monomethyl fumarate," Shipin Gongye Keji (2008), 29(6), pp. 259-262.

Zheng et al., "Improved Preparation of Monomethyl Fumarate," Huaxue Shijie (2004), 45(4), pp. 207-208, 217.

Zhu et al., Inhibition of dendritic cell differentiation by fumaric acid esters, J. Invest. Dermatol. (2001), 116: 203-208.

The Engineering Tool Box, "Acids—pH Values," <http://www.engineeringtoolbox.com/acids-ph-d_401.html>, published Feb. 24, 2006, pp. 1-2.

Steckel et al., "The extrusion and speronization of chitosan," Pharmaceutical Technology Europe, <http://www.pharmtech.com/extrusion-and-spheronization-chitosan>, published Jul. 2, 2007, pp. 1-12.

Mannervik et al., "Identification of three classes of cytosolic glutathione transferase common to several mammalian species: Correlation between structural data and enzymatic properties," Proc. Natl. Acad. Sci., USA, Nov. 1985, vol. 82, pp. 7202-7206.

Sheikh, et al., "Safety Tolerability and Pharmacokinetics of BG-12 Administered with and without Aspirin, Key Findings from a Randomized, Double-blind, placebo-controlled trial in healthy volunteers", Poster P04.136 presented at the 64th Annual Meeting of the American Academy of Neurology, Apr. 21-28, 2012, New Orleans, LA, 2 pp.

Dawson et al., "Bioequivalence of BG-12 (Dimethyl Fumarate) Administered as a Single 240 mg Capsule and Two 120 mg Capsules: Findings from a Randomized, Two-period Crossover Study", Poster P913 presented at the 28th Congress of the European Committee for Treatment and Research in Multiple Sclerosis, Oct. 10-13, 2012, Lyon France, 1 p.

Woodworth et al., "Pharmacokinetics of Oral BG-12 Alone Compared with BG-12 and Interferon B-1a or Glatiramer Acetate Administered Together, Studied in Healthy Volunteers", Poster P04.207 presented at the 62nd Annual Meeting of the American Academy of Neurology, Apr. 10-17, 2010, Toronto, Ontario, Canada, 2 pages.

Mrowietz, et al., "Dimethylfumarate for psoriasis: more than a dietary curiosity", Trends in Molecular Medicine, vol. 11, No. 1, Jan. 2005, pp. 43-48.

Yazdi et al., "Fumaric acid esters," Clinics in Dermatology (2008), 26, pp. 522-526.

(56) References Cited

OTHER PUBLICATIONS

Lehmann et al., Fumaric acid esters are potent immunosuppressants: inhibition of acute and chronic rejection in rat kidney transplantation models by methyl hydrogen fumarate. Arch Dermatol Res (2002), 294, pp. 399-404.

Schimrigk, et al., "Oral fumaric acid esters for the treatment of active multiple sclerosis: an open-label, baseline-controlled pilot study", European Journal of Neurology, 2006, 13: pp. 604-610.

Schilling, et al., "Fumaric acid esters are effective in chronic experimental autoimmune encephalomyelitis and suppress macrophage infiltration", Clinical and Experimental Immunology, 2006, 145: pp. 101-107.

Dymicky, "Preparation of Monomethyl Fumarate," Organic Preparations and Procedures International, vol. 15 No. 4 (1983), pp. 233-238.

Spatz, et al., Methyl Hydrogen Fumarate, Journal of Organic Chemistry, 1958, 23 (10), pp. 1559-1560.

Food and Drug Administration—Department of Health and Human Services; "International Conference on Harmonisation; Guidelines for the Photostability Testing of New Drug Substances and Products; Availability; Notice," Federal Register, vol. 62, No. 95; May 16, 1997, pp. 27115-27122.

Griffin, et al., The Chemistry of Photodimers of Maleic and Fumaric Acid Derivatives. I. Dimethyl Fumarate Dimer; J. Am. Chem. Soc. (1961), 83: pp. 2725-2728.

Jamil, et al., "Studies of Photostability of Reserpine in Parenteral Solutions," Die Pharmazie (1983), 38: pp. 467-469.

Killestein, et al., "Oral treatment for multiple sclerosis," Lancet Neurology, Lancet Publishing Group, London, GB, vol. 10, No. 11, Nov. 2011, pp. 1026-1034.

Bhattacharya et al., Polymorphism in Pharmaceutical Solids: Thermoanalytical and Crystallographic Methods 334 (Brittain H. ed., 2d ed. Informa Healthcare USA, Inc. 2009) (1999), 20 pp.

Ivanisevic et al., "Uses of X-Ray Powder Diffraction in the Pharmaceutical Industry," Pharmaceutical Formulation & Quality, 32 (2011), pp. 30-33.

Gogas et al., "Comparison of the efficacy and tolerability of a novel methyl hydrogen fumarate prodrug with dimethyl fumarate in rodent EAE and GI irritation models," Multiple Sclerosis, 2010, vol. 16, No. 10 Supplement, pp. S230-S231.

Dow, "Methocel Cellulose Technical Handbook", <http://www.dow.com/dowwolff/en/pdf/192-01062.pdf>, 2002, 32 pages.

Carter et al., Chemotherapy of Cancer, 2nd ed., 1981, pp. 362-365.

U.S. Appl. No. 14/990,582, filed Jan. 7, 2016, Karaborni et al.

General pharmaceutics (5th edition), 1997, 5 pages, published in Japan.

Tammara et al., "Morpholinoalkyl Ester Prodrugs of Diclofenac: Synthesis, In Vitro and In Vivo Evaluation," Journal of Pharmaceutical Sciences, 1994 vol. 83, No. 5, pp. 644-648.

General pharmaceutics (5th edition) with partial translation of pp. 208-209, 1997, 5 pages, published in Japan.

Compound (CAS RN 473669-27-1) entered STN chemical database on Nov. 15, 2002 by Ambinter, 4 pp.

Booth et al., "Regulation of dimethyl-fumarate toxicity by proteasome inhibitors," Cancer Biology & Therapy, Dec. 2014, vol. 15(12), pp. 1646-1657.

Silhavy et al., "Fumaric Acid Esters Can Block Pro-Inflammatory Actions of Human CRP and Ameliorate Metabolic Disturbances in Transgenic Spontaneously Hypertensive Rats," PLOS One, Jul. 2014, vol. 9, Issue 7, e101906, pp. 1-9.

\* cited by examiner

PHARMACEUTICAL COMPOSITIONS OF DIMETHYL FUMARATE

CROSS REFERENCE TO RELATED APPLICATIONS

This application claims the benefit of the filing date under 35 U.S.C. § 119 of U.S. Provisional Patent Application Ser. No. 61/804,725, filed Mar. 24, 2013; of U.S. Provisional Patent Application Ser. No. 61/805,137, filed Mar. 25, 2013; of U.S. Provisional Patent Application Ser. No. 61/805,516, filed Mar. 26, 2013; and of U.S. Provisional Patent Application Ser. No. 61/805,869, filed Mar. 27, 2013; each of which is herein incorporated by reference in their entirety for all purposes.

TECHNICAL FIELD

Disclosed herein are pharmaceutical compositions of dimethyl fumarate having low levels of undesirable impurities.

BACKGROUND

Dimethyl fumarate, also known by the acronym DMF, is the dimethyl ester of fumaric acid. The compound has a molecular weight of 144.13 daltons and the following chemical structure:

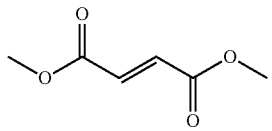

DMF is also known by the names Dimethyl (E)-butenedioate (IUPAC), trans-1,2-Ethylenedicarboxylic acid dimethyl ester and (E)-2-Butenedioic acid dimethyl ester. DMF is typically synthesized by reacting fumaric acid with excess methanol in the presence of an acid catalyst. DMF can also be synthesized according to the methods described in Chinese Patent Publication CN 101318901A.

Fumaderm®, an enteric coated tablet containing a mixture of salts of monoethyl fumarate and dimethyl fumarate was approved in Germany in 1994 for the treatment of psoriasis. Fumaderm® is dosed three times per day with 1-2 grams/day administered for the treatment of psoriasis.

Biogen Idec's BG-12 product, a delayed release (i.e., enteric coated microtablets) oral dosage form of dimethyl fumarate, has been in clinical testing for the treatment of multiple sclerosis. Details concerning the clinical testing of BG-12 are disclosed in Sheikh et al., Safety Tolerability and Pharmacokinetics of BG-12 Administered with and without Aspirin, Key Findings from a Randomized, Double-blind, Placebo-controlled Trial in Healthy Volunteers, Poster PO4.136 presented at the 64th Annual Meeting of the American Academy of Neurology, Apr. 21-28, 2012, New Orleans, La.; Dawson et al., Bioequivalence of BG-12 (Dimethyl Fumarate) Administered as a Single 240 mg Capsule and Two 120 mg Capsules: Findings from a Randomized, Two-period Crossover Study, Poster P913 presented at the 28th Congress of the European Committee for Treatment and Research in Multiple Sclerosis, Oct. 10-13, 2012, Lyon, France; and Woodworth et al., Pharmacokinetics of Oral BG-12 Alone Compared with BG-12 and Interferon β-1a or Glatiramer Acetate Administered Together, Studied in Health Volunteers, Poster PO4.207 presented at the 62nd Annual Meeting of the American Academy of Neurology, Apr. 10-17, 2010, Toronto, Ontario, Canada.

DMF and/or other fumaric acid esters have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., Arch Dermatol Res 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

Pharmaceutical compositions containing DMF and other fumaric acid esters, and/or methods of treatment using same, are disclosed in Joshi et al. U.S. Pat. No. 6,277,882; Joshi et al. U.S. Pat. No. 6,355,676; Joshi et al. U.S. Pat. No. 6,359,003; Joshi et al. U.S. Pat. No. 6,436,992; Joshi et al. U.S. Pat. No. 6,509,376; Joshi et al. U.S. Pat. No. 6,858,750; Joshi et al U.S. Pat. No. 7,320,999; Joshi et al. U.S. Pat. No. 7,612,110; Joshi et al. U.S. Pat. No. 7,619,001; Joshi et al. U.S. Pat. No. 7,803,840; Joshi et al. U.S. Pat. No. 7,915,310; Joshi et al. US 2011/0293711; Joshi et al. US 2011/0124615; Lukashev US 2011/0112196; Nilsson et al. US 2008/0299196; Went et al. US 2008/0089861; Nilsson et al. WO 2007/042034; Nilsson et al. US 2012/0034274; and Nilsson et al. US 2012/0034303.

Many pharmaceutically active agents are susceptible to photodegradation upon exposure to sunlight and/or UV light. Generally, incorporation of light absorbers into formulations can stabilize these photosensitive agents to some extent. For example, N. Jamil et al. ("Studies of the photostability of reserpine in parenteral solutions", Die Pharmazie, 38: 467-469 (1983)), refers to studies done on the photostability of reserpine in parenteral formulations and the effects of some commonly used stabilizers. U.S. Pat. No. 6,379,697, titled "Stabilization of photosensitive materials" to Gregoriadis, et al. refers to liposomes containing a photosensitive material together with a light absorbing material capable of increasing the photostability of the photosensitive material.

Griffin et al. ("The chemistry of photodimers of maleic and fumaric acid derivatives. I. Dimethyl fumarate dimer", J Am Chem Soc (1961), 83: 2725-2728), disclose that dimethyl fumarate degrades in the presence of light to form the photodimer compound tetramethyl cyclobutane-1,2,3,4-tetracarboxylate (compound (1)) disclosed herein. See also Griffin et al. U.S. Pat. No. 3,139,395.

SUMMARY

Thus, in a first aspect, a dosage form for treating multiple sclerosis is provided, comprising: (a) a therapeutically effective amount of dimethyl fumarate in solid form; (b) one or more compounds of Formula (I):

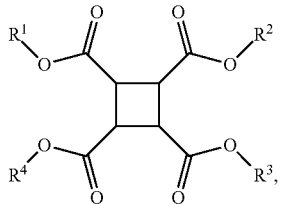

(I)

isomers thereof, and salts of any of the foregoing, wherein:
each of $R^1$ through $R^4$ is independently chosen from hydrogen and methyl; and
wherein the one or more compounds of Formula (I) are present in the dosage form in a combined total amount of less than 2% by weight based on the total weight of the dimethyl fumarate; and (c) a pharmaceutically acceptable vehicle.

In some embodiments, the one or more compounds of Formula (I) are present in a combined total amount of less than about 2% by weight based on the total weight of the dimethyl fumarate.

In some embodiments, the one or more compounds of Formula (I) are present in a combined total amount of less than about 1% by weight based on the total weight of the dimethyl fumarate.

In some embodiments, each of the one or more compounds is present in an amount of less than about 0.3% by weight based on the total weight of the dimethyl fumarate.

In some embodiments, each of the one or more compounds of Formula (I) is present in an amount of less than about 0.2% by weight based on the total weight of the dimethyl fumarate.

In some embodiments, each of the one or more compounds of Formula (I) is present in an amount of less than about 0.1% by weight based on the total weight of the dimethyl fumarate.

In a second aspect, a dosage form for treating multiple sclerosis is provided, comprising: (a) a therapeutically effective amount of dimethyl fumarate in solid form; (b) one or more compounds of Formula (II):

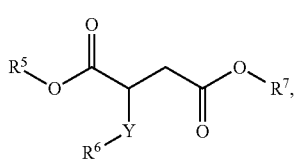

(II)

isomers thereof, and salts of any of the foregoing; wherein:
each of $R^5$ and $R^7$ is independently chosen from hydrogen and methyl;
Y is chosen from O, S, NH and $NR^8$;
$R^6$ is chosen from hydrogen, lower alkyl and aryl;
$R^8$ is chosen from lower alkyl; and
wherein the one or more compounds of Formula (II) are present in a combined total amount of less than 3% by weight based on total weight of the dimethyl fumarate; and (c) a pharmaceutically acceptable vehicle.

In some embodiments, the one or more compounds of Formula (II) are present in a combined total amount of less than about 2% by weight based on the total weight of the dimethyl fumarate.

In some embodiments, the one or more compounds of Formula (II) are present in a combined total amount of less than about 1% by weight based on the total weight of the dimethyl fumarate.

In some embodiments, each of the one or more compounds of Formula (II) is present in an amount of less than about 0.3% by weight based on the total weight of the dimethyl fumarate.

In some embodiments, each of the one or more compounds of Formula (II) is present in an amount of less than about 0.2% by weight based on the total weight of the dimethyl fumarate.

In some embodiments, each of the one or more compounds of Formula (II) is present in an amount of less than about 0.1% by weight based on the total weight of the dimethyl fumarate.

In some embodiments, the composition comprising DMF and the one or more compounds of Formula (II) are substantially free of any alcohols, mercaptans, and amino compounds.

Dimethyl fumarate (DMF) has been found to be susceptible to oxidation, whether in solid crystalline form or in aqueous solution. Oxidation of DMF results in the formation of compounds of Formula (III):

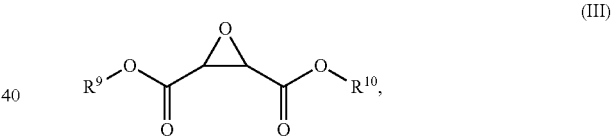

(III)

wherein each $R^9$ and $R^{10}$ is independently chosen from hydrogen and methyl.

Further, the oxidation of DMF, and the resulting formation of compound(s) of Formula (III), are substantially increased in the presence of either polyvinyl pyrrolidones (PVPs), polyethylene glycols (PEGs) and/or polysorbate surfactants. Since the concentration of DMF employed in dosage forms (e.g., solid oral dosage forms) is typically only about 50 wt % and sometimes less, and other components of the formulation (which may be destabilizing) are present in similar concentrations as DMF itself, there is a particular concern with the oxidation of DMF.

Thus, in a third aspect, a pharmaceutical composition is provided, comprising (a) dimethyl fumarate in solid form; and (b) one or more compounds of Formula (III):

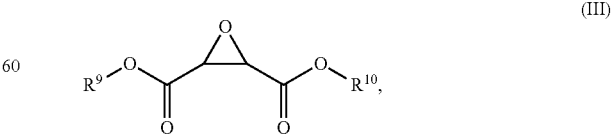

(III)

isomers thereof, and salts of any of the foregoing, wherein:
each $R^9$ and $R^{10}$ is independently chosen from hydrogen and methyl; and wherein each individual compounds of Formula (III) is present in an amount of less than 15 ppm based on the total weight of the dimethyl fumarate.

In another aspect, a dosage form for treating multiple sclerosis is provided, comprising (a) dimethyl fumarate in solid form; and (b) one or more compounds of Formula (III):

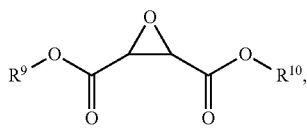

isomers thereof, and salts of any of the foregoing, wherein:

each $R^9$ and $R^{10}$ is independently chosen from hydrogen and methyl; and wherein each individual compounds of Formula (III) is present in an amount of less than 15 ppm based on the total weight of the dimethyl fumarate; and (c) a pharmaceutically acceptable vehicle.

In some embodiments of the pharmaceutical composition and/or the dosage form, the one or more compounds of Formula (III) are present in a combined total amount of less than 15 ppm based on the total weight of the dimethyl fumarate. In some embodiments, the one or more compounds of Formula (III) are present in a combined total amount of less than 10 ppm based on the total weight of the dimethyl fumarate.

In some embodiments of the pharmaceutical composition and/or the dosage form, each of the one or more compounds of Formula (III) is present in an amount selected from less than about 15 ppm, less than about 10 ppm, less than about 8 ppm, and less than about 5 ppm, based on the total weight of the dimethyl fumarate.

In some embodiments of the pharmaceutical composition and/or the dosage form, the pharmaceutical composition comprising DMF and the one or more compounds of Formula (III) is substantially free of PVP, PEG and/or polysorbate surfactant.

In some embodiments, the pharmaceutical composition comprising DMF and the one or more compounds of Formula (III) is a dosage form, comprising a therapeutically effective amount of DMF and a pharmaceutically acceptable vehicle.

In a fourth aspect, a dosage form for treating multiple sclerosis is provided, comprising: (a) a therapeutically effective amount of dimethyl fumarate in solid form; (b) one or more compounds of Formula (IV):

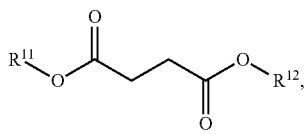

isomers thereof, and salts of any of the foregoing, wherein:

each of $R^{11}$ and $R^{12}$ is independently chosen from hydrogen and methyl; and wherein the one or more compounds of Formula (IV) are present in a combined total amount of less than 2% by weight based on total weight of the dimethyl fumarate; and (c) a pharmaceutically acceptable vehicle.

In some embodiments, the one or more compounds of Formula (IV) are present in a combined total amount of less than about 2% by weight based on the total weight of the dimethyl fumarate.

In some embodiments, the one or more compounds of Formula (IV) are present in a combined total amount of less than about 1% by weight based on the total weight of the dimethyl fumarate.

In some embodiments, each of the one or more compounds of Formula (IV) is present in an amount of less than about 0.3% by weight based on the total weight of the dimethyl fumarate.

In some embodiments, each of the one or more compounds of Formula (IV) is present in an amount of less than about 0.2% by weight based on the total weight of the dimethyl fumarate.

In some embodiments, each of the one or more compounds of Formula (IV) is present in an amount of less than about 0.1% by weight based on the total weight of the dimethyl fumarate.

In a fifth aspect, a dosage form for treating multiple sclerosis is provided, comprising: (a) a therapeutically effective amount of dimethyl fumarate in solid form; (b) one or more compounds of Formula (V):

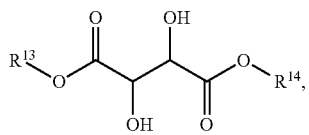

isomers thereof, and salts of any of the foregoing; wherein:

each of $R^{13}$ and $R^{14}$ is independently chosen from hydrogen and methyl; and wherein the one or more compounds of Formula (V) are present in a combined total amount of less than 2% by weight based on total weight of the dimethyl fumarate; and (c) a pharmaceutically acceptable vehicle.

In some embodiments, the one or more compounds of Formula (V) are present in a combined total amount of less than about 2% by weight based on the total weight of the dimethyl fumarate.

In some embodiments, the one or more compounds of Formula (V) are present in a combined total amount of less than about 1% by weight based on the total weight of the dimethyl fumarate.

In some embodiments, each of the one or more compounds of Formula (V) is present in an amount of less than about 0.3% by weight based on the total weight of the dimethyl fumarate.

In some embodiments, each of the one or more compounds of Formula (V) is present in an amount of less than about 0.2% by weight based on the total weight of the dimethyl fumarate.

In some embodiments, each of the one or more compounds of Formula (V) is present in an amount of less than about 0.1% by weight based on the total weight of the dimethyl fumarate.

In a sixth aspect, a dosage form for treating multiple sclerosis is provided, comprising: (a) a therapeutically effective amount of dimethyl fumarate in solid form; (b) one or more compounds of Formula (VI):

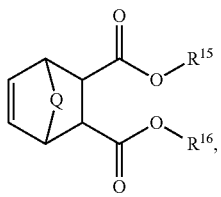

(VI)

isomers thereof, and salts of any of the foregoing, wherein:

Q is —O—, —S—, —NH—, or —N($R^{17}$)— or —C($R^{18}$)$_2$—;

each of $R^{15}$ and $R^{16}$ is independently chosen from hydrogen and methyl;

$R^{17}$ is alkyl;

each $R^{18}$ is independently hydrogen or alkyl; and wherein the one or more compounds of Formula (VI) are present in a combined total amount of less than 2% by weight based on total weight of the dimethyl fumarate; and (c) a pharmaceutically acceptable vehicle.

In some embodiments, the one or more compounds of Formula (VI) are present in a combined total amount of less than about 2% by weight based on the total weight of the dimethyl fumarate.

In some embodiments, the one or more compounds of Formula (VI) are present in a combined total amount of less than about 1% by weight based on the total weight of the dimethyl fumarate.

In some embodiments, each of the one or more compounds of Formula (VI) is present in an amount of less than about 0.3% by weight based on the total weight of the dimethyl fumarate.

In some embodiments, each of the one or more compounds of Formula (VI) is present in an amount of less than about 0.2% by weight based on the total weight of the dimethyl fumarate.

In some embodiments, each of the one or more compounds of Formula (VI) is present in an amount of less than about 0.1% by weight based on the total weight of the dimethyl fumarate.

The compositions and dosage forms disclosed herein can be used to treat any number of diseases for which FAEs are known or thought to be therapeutically effective. In several aspects, the compositions and dosage forms disclosed herein can be used to treat multiple sclerosis and psoriasis.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification and the drawings, which forms a part of this disclosure.

FIGURES

The present disclosure may be understood by reference to the following detailed description, taken in conjunction with the drawings as described below. It is noted that, for purposes of illustrative clarity, certain elements in various drawings may not be drawn to scale, may be represented schematically or conceptually, or otherwise may not correspond exactly to certain physical configurations of embodiments.

DEFINITIONS

Figure 1:
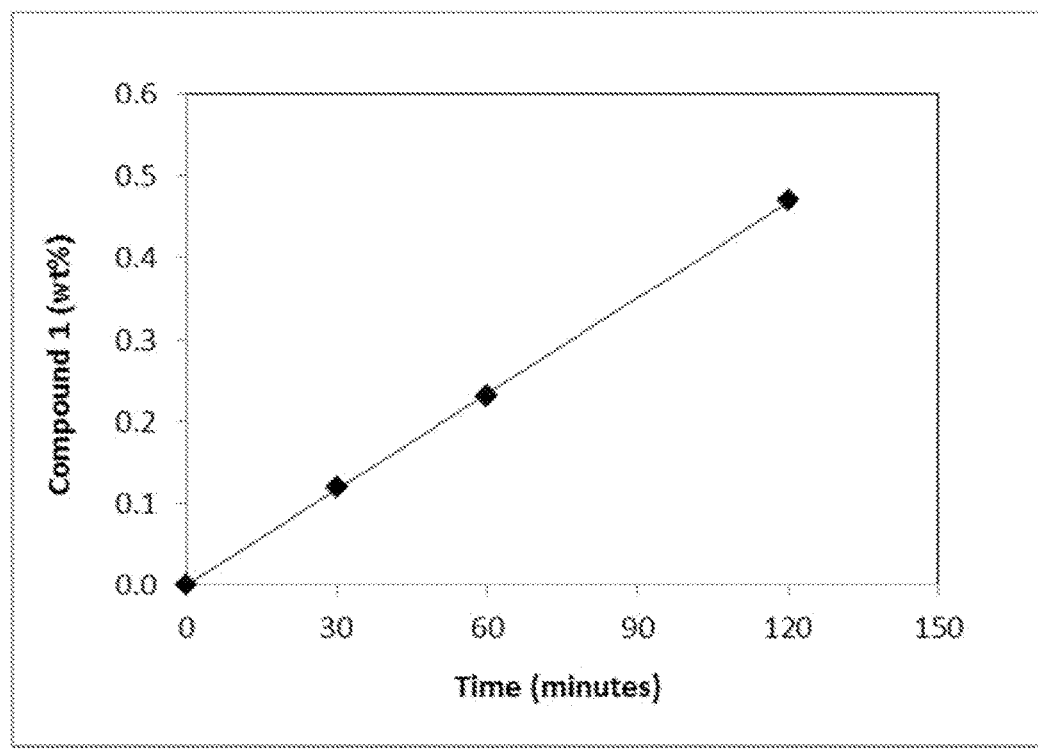
FIG. 1 shows the formation of compound (1) after DMF powder has been exposed to fluorescent light for 2 hours.

A dash ("-") that is not between two letters or symbols is used to indicate a point of attachment for a moiety or substituent. For example, —CONH$_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-8}$), and in certain embodiments, from 1 to 3 carbon atoms ($C_{1-3}$).

The term "alkyl" is specifically intended to include lower alkyl groups. As used herein, the phrase "lower alkyl" refers to a saturated or unsaturated, branched, or straight-chain, monovalent hydrocarbon radical of six or fewer carbon atoms, derived by the removal of one hydrogen atom from a single carbon atom of a parent alkane, alkene, or alkyne. In certain embodiments, a lower alkyl group can have from 1 to 6 carbon atoms ($C_{1-6}$), in certain embodiments from 1 to 5 carbon atoms ($C_{1-5}$), in certain embodiments from 1 to 4 carbon atoms ($C_{1-4}$), in certain embodiments, from 1 to 3 carbon atoms ($C_{1-3}$), in certain embodiments from 1 to 2 carbon atoms ($C_{1-2}$) and in certain embodiments a single carbon atom. Examples of lower alkyl groups include, but are not limited to, methyl, ethyl, propyl, n-propyl, isopropyl, butyl, isobutyl, n-butyl, sec-butyl, tert-butyl, pentyl, isopentyl, hexyl, isohexyl, etc., and the like.

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{1-10}$), and in certain embodiments from 6 to 8 carbon atoms ($C_{6-8}$). Aryl, however, does not encompass or overlap in any way with heteroaryl, separately defined herein.

"Compounds" refers to chemical substances consisting of two or more different chemical elements that can be separated into simpler substances by chemical reactions. Compounds have a unique and defined chemical structure; they consist of a fixed ratio of atoms that are held together in a defined spatial arrangement by chemical bonds. Compounds include any specific compounds within a given chemical formula. Compounds may be identified either by their chemical structure and/or chemical name. Compounds are named using Chemistry 4-D Draw Pro, version 7.01c (Cheminnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompasses all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds include, but are not limited to, optical isomers, racemates, and other mixtures. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Notwithstanding the foregoing, in the compounds monomethyl fumarate and dimethyl fumarate, the configuration of the illustrated double bond is only in the E configuration (i.e. trans configuration).

Compounds may also exist in several tautomeric forms including the enol form, the keto form, and mixtures thereof. Accordingly, the chemical structures depicted herein encompass all possible tautomeric forms of any illustrated compounds. Compounds also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds as referred to herein may be free acid, hydrated, solvated, or N-oxides. Compounds may exist in one or more ionic forms. Certain compounds may exist in multiple crystalline, co-crystalline, or amorphous forms. Compounds include pharmaceutically acceptable salts, or pharmaceutically acceptable solvates of the free acid form of any of the foregoing, as well as crystalline forms of any of the foregoing.

Compounds also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of compounds are illustrated, an asterisk (*) indicates the point of attachment of the partial structure to the rest of the molecule.

"Dimethyl fumarate" refers to the dimethyl ester of fumaric acid. The compound has a molecular weight of 144.13 daltons and the following chemical structure:

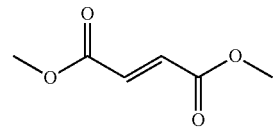

This compound is also known by the names Dimethyl (E)-butenedioate (IUPAC), trans-1,2-Ethylenedicarboxylic acid dimethyl ester and (E)-2-Butenedioic acid dimethyl ester. The compound is also referred to by the acronym DMF. DMF can be synthesized according to the methods described in Chinese Patent Publication CN 101318901A, the disclosures of which are incorporated herein by reference.

"Disease" refers to a disease, disorder, condition, or symptom of any of the foregoing.

"Drug" as defined under 21 U.S.C. § 321(g)(1) means (A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals.

"Monomethyl fumarate" refers to the monomethyl ester of fumaric acid. The compound has a molecular weight of 130.10 daltons and the following chemical formula:

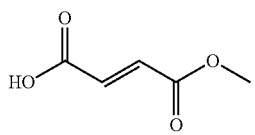

The compound is also commonly referred to as 2(E)-Butenedioic acid 1-methyl ester; (2E)-4-Methoxy-4-oxobut-2-enoic acid; Fumaric acid hydrogen 1-methyl ester; (2E)-2-Butenedioic acid 1-methyl ester; (E)-2-Butenedioic acid monomethyl ester; Monomethyl trans-ethylene-1,2-dicarboxylate; and methyl hydrogen fumarate. The compound is also referred to herein and elsewhere by the acronyms MMF and/or MHF. MMF can be synthesized according to the methods described in Dymicky, Preparation of Monomethyl Fumarate, Organic Preparations and Procedures International: The New Journal for Organic Synthesis, Vol 14, Issue 4, 1983; and Spatz et al., J. Org. Chem., 1958, 23 (10), 1559-1560.

"Multiple sclerosis" also known as "disseminated sclerosis" or "encephalomyelitis disseminata", and sometimes referred to by the acronym MS, is an inflammatory disease in which the fatty myelin sheaths around the axons of the brain and spinal cord are damaged, leading to demyelination and scarring as well as a broad spectrum of signs and symptoms. Disease onset usually occurs in young adults, and it is more common in women. It has a prevalence that ranges between 2 and 150 per 100,000.

MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. The name multiple sclerosis refers to scars (sclerae-better known as plaques or lesions) particularly in the white matter of the brain and spinal cord, which is mainly composed of myelin. Although much is known about the mechanisms involved in the disease process, the cause remains unknown. Theories include genetics or infections. Different environmental risk factors have also been found.

Almost any neurological symptom can appear with the disease, and the disease often progresses to physical and cognitive disability. MS takes several forms, with new symptoms occurring either in discrete attacks (relapsing forms) or accumulating over time (progressive forms). Between attacks, symptoms may go away completely, but permanent neurological deficits often occur, especially as the disease advances.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient, which does not destroy the pharmacological activity thereof and which is non-toxic when administered in doses sufficient to provide a therapeutically effective amount of the compound.

"Pharmaceutical composition" refers to a therapeutically active compound and at least one pharmaceutically acceptable vehicle, with which the compound is administered to a patient.

"Polyethylene glycol" and "PEG" each refer to a linear polymer formed by the addition reaction of ethylene glycol with ethylene oxide. PEG is commercially available in average molecular weights ranging from about 200 to greater than 20,000. The commercially available grades of polyethylene glycol are marketed based on the average molecular weight, e.g., the grade nomenclature is identified with the molecular weight. For example, PEG 400 represents material with an average molecular weight of 400 and the material with an average molecular weight of 600 is known as PEG 600. PEG 200, 300, 400, and 600 are clear viscous liquids at room temperature; PEG 900, 1000, 1450, 3350, 4500 and 8000 are white, waxy solids.

"Polyvinylpyrrolidone" and "PVP" each refer to a linear polymer of 1-vinyl-2-pyrrolidone. PVP, also known as Povidone, is commercially available as a series of products having mean molecular weights ranging from about 10,000 to about 700,000. The various products are marketed according to average molecular weights designated K-values; e.g., GAF Corporation supplies PVP having K-value=15 as having an average molecular weight of about 10,000, and K-value=30 as having an average molecular weight of about 40.000.

"Psoriasis" is an immune-mediated disease that affects the skin. It is typically a lifelong condition. Psoriasis occurs when the immune system mistakes a normal skin cell for a pathogen, and sends out faulty signals that cause overproduction of new skin cells. There are five types of psoriasis: plaque, guttate, inverse, pustular, and erythrodermic. The most common form, plaque psoriasis, is commonly seen as red and white hues of scaly patches appearing on the top first layer of the epidermis (skin). Some patients, though, have no dermatological signs or symptoms. The name psoriasis is from the Greek word, meaning roughly "itching condition" (psora "itch"+-sis "action, condition").

In plaque psoriasis, skin rapidly accumulates at these sites, which gives it a silvery-white appearance. Plaques frequently occur on the skin of the elbows and knees, but can affect any area, including the scalp, palms of hands and soles of feet, and genitals. In contrast to eczema, psoriasis is more likely to be found on the outer side of the joint.

The disorder is a chronic recurring condition that varies in severity from minor localized patches to complete body coverage. Fingernails and toenails are frequently affected (psoriatic nail dystrophy) and can be seen as an isolated sign. Psoriasis can also cause inflammation of the joints, which is known as psoriatic arthritis. Between 10% and 30% of all people with psoriasis also have psoriatic arthritis.

The cause of psoriasis is not fully understood, but it is believed to have a genetic component and local psoriatic changes can be triggered by an injury to the skin known as the Koebner phenomenon. Various environmental factors have been suggested as aggravating to psoriasis, including oxidative stress, stress, withdrawal of systemic corticosteroid, as well as other environmental factors, but few have shown statistical significance.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

DETAILED DESCRIPTION

Reference is now made in detail to certain embodiments of pharmaceutical compositions of monomethyl fumarate. The disclosed embodiments are not intended to be limiting of the claims. To the contrary, the claims are intended to cover all alternatives, modifications, and equivalents.

Regulatory authorities worldwide require the amounts of impurities to be maintained at the lowest possible levels in pharmaceutical compositions and formulations. Hence there exists a need for stabilized compositions of DMF.

DMF in pure stable crystalline form is available for sale commercially from a number of sources. One source is Tokyo Chemical Industry Co., Ltd. (TCI) which has offices in the United States in Portland, Oreg.

If exposed to sufficient amounts of light or if sufficiently exposed to an oxidant, DMF is prone to a number of reactions such as oxidative stress and photodegradation, which gives rise to impurities. Two of several impurities which can be generated are tetramethyl cyclobutane-1,2,3,4-tetracarboxylate formed by photodegradation of DMF and dimethyl oxirane-2,3-dicarboxylate formed by oxidation of DMF.

In a first aspect, a dosage form for treating multiple sclerosis is provided which comprises (a) a therapeutically effective amount of dimethyl fumarate in solid form; (b) one or more cyclobutane compounds of Formula (I):

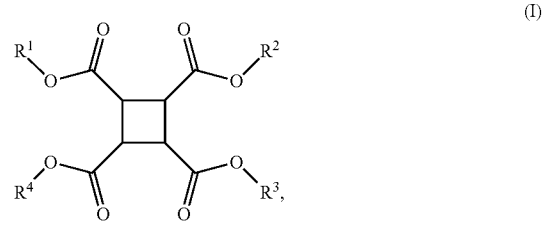

isomers thereof, and salts of any of the foregoing, wherein:

each of $R^1$ through $R^4$ is independently chosen from hydrogen and methyl; and wherein the one or more compounds of Formula (I) are present in a total combined amount of less than 2% by weight based on total weight of the dimethyl fumarate; and (c) a pharmaceutically acceptable vehicle.

In some embodiments, the dimethyl fumarate is in crystalline form. In some embodiments, the dimethyl fumarate is in amorphous form.

In some embodiments, the one or more compounds of Formula (I) are present in a combined total amount of less than about 2% by weight based on the total weight of the dimethyl fumarate. In some embodiments, the one or more compounds of Formula (I) are present in a combined total amount of less than about 1.8% by weight based on the total weight of the dimethyl fumarate. In some embodiments, the one or more compounds of Formula (I) are present in a combined total amount of less than about 1.6% by weight based on the total weight of the dimethyl fumarate. In some embodiments, the one or more compounds of Formula (I) are present in a combined total amount of less than about 1.4% by weight based on the total weight of the dimethyl fumarate. In some embodiments, the one or more compounds of Formula (I) are present in a combined total amount of less than about 1.2% by weight based on the total weight of the dimethyl fumarate. In some embodiments, the one or more compounds of Formula (I) are present in a combined total amount of less than about 1.0% by weight based on the total weight of the dimethyl fumarate. In some embodiments, the one or more compounds of Formula (I)

are present in a combined total amount of less than about 0.8% by weight based on the total weight of the dimethyl fumarate. In some embodiments, the one or more compounds of Formula (I) are present in a combined total amount of less than about 0.6% by weight based on the total weight of the dimethyl fumarate. In some embodiments, the one or more compounds of Formula (I) are present in a combined total amount of less than about 0.4% by weight based on the total weight of the dimethyl fumarate. In some embodiments, the one or more compounds of Formula (I) are present in a combined total amount of less than about 0.2% by weight based on the total weight of the dimethyl fumarate. In some embodiments, the one or more compounds of Formula (I) are present in a combined total amount of less than about 0.1% by weight based on the total weight of the dimethyl fumarate.

In some embodiments, the one or more compounds of Formula (I) are present in a combined total amount of about 0.001% to 2% by weight based on the total weight of the dimethyl fumarate. In some embodiments, the one or more compounds of Formula (I) are present in a combined total amount of about 0.001% to 1.8% by weight based on the total weight of the dimethyl fumarate. In some embodiments, the one or more compounds of Formula (I) are present in a combined total amount of about 0.001% to 1.6% by weight based on the total weight of the dimethyl fumarate. In some embodiments, the one or more compounds of Formula (I) are present in a combined total amount of about 0.001% to 1.4% by weight based on the total weight of the dimethyl fumarate. In some embodiments, the one or more compounds of Formula (I) are present in a combined total amount of about 0.001% to 1.2% by weight based on the total weight of the dimethyl fumarate. In some embodiments, the one or more compounds of Formula (I) are present in a combined total amount of about 0.001% to 1.0% by weight based on the total weight of the dimethyl fumarate. In some embodiments, the one or more compounds of Formula (I) are present in a combined total amount of about 0.001% to 0.8% by weight based on the total weight of the dimethyl fumarate. In some embodiments, the one or more compounds of Formula (I) are present in a combined total amount of about 0.001% to 0.6% by weight based on the total weight of the dimethyl fumarate. In some embodiments, the one or more compounds of Formula (I) are present in a combined total amount of about 0.001% to 0.4% by weight based on the total weight of the dimethyl fumarate. In some embodiments, the one or more compounds of Formula (I) are present in a combined total amount of about 0.001% to 0.2% by weight based on the total weight of the dimethyl fumarate. In some embodiments, the one or more compounds of Formula (I) are present in a combined total amount of about 0.001% to 0.1% by weight based on the total weight of the dimethyl fumarate.

In some embodiments, the one or more compounds of Formula (I) are present in a total combined amount of less than about 2% by weight based on total weight of the dimethyl fumarate. In some embodiments, the one or more compounds of Formula (I) are present in a total combined amount of less than about 1% by weight based on total weight of the dimethyl fumarate.

Compounds of Formula (I) include tetramethyl cyclobutane-1,2,3,4-tetracarboxylate (compound (1)), in which $R^1$ through $R^4$ are all methyl; 3,4-bis(methoxycarbonyl)cyclobutane-1,2-dicarboxylic acid, in which $R^1$ and $R^2$ are each hydrogen and $R^3$ and $R^4$ are each methyl; 2,4-bis (methoxycarbonyl)cyclobutane-1,3-dicarboxylic acid, in which $R^1$ and $R^3$ are each hydrogen and $R^2$ and $R^4$ are each methyl; and cyclobutane-1,2,3,4-tetracarboxylic acid, in which $R^1$ through $R^4$ are all hydrogen; as well as isomers thereof, and salts of any of the foregoing.

In some embodiments, the isomers of compounds of Formula (I) include, 1R,2R,3R,4R-, 1S,2S,3S,4S-, 1R,2R,3S,4S-, or 1R,2S,3R,4S-isomers.

In some embodiments, the compounds of Formula (I) include 1R,2R,3S,4S-isomers.

In some embodiments, each of the one or more compounds of Formula (I) is present in an amount of less than about 0.3% by weight based on the total weight of the dimethyl fumarate. In some embodiments, each of the one or more compounds of Formula (I) is present in an amount of less than about 0.2% by weight based on the total weight of the dimethyl fumarate. In some embodiments, each of the one or more compounds of Formula (I) is present in an amount of less than about 0.15% by weight based on the total weight of the dimethyl fumarate. In some embodiments, each of the one or more compounds of Formula (I) is present in an amount of less than about 0.1% by weight based on the total weight of the dimethyl fumarate. In some embodiments, each of the one or more compounds of Formula (I) is present in an amount of less than about 0.05% by weight based on the total weight of the dimethyl fumarate.

In some embodiments, each of the one or more compounds of Formula (I) is present in an amount of about 0.001% to 0.3% by weight based on the total weight of the dimethyl fumarate. In some embodiments, each of the one or more compounds of Formula (I) is present in an amount of about 0.001% to 0.2% by weight based on the total weight of the dimethyl fumarate. In some embodiments, each of the one or more compounds of Formula (I) is present in an amount of about 0.001% to 0.15% by weight based on the total weight of the dimethyl fumarate. In some embodiments, each of the one or more compounds of Formula (I) is present in an amount of about 0.001% to 0.1% by weight based on the total weight of the dimethyl fumarate. In some embodiments, each of the one or more compounds of Formula (I) is present in an amount of about 0.001% to 0.05% by weight based on the total weight of the dimethyl fumarate.

Compounds of Formula (I) are known photodegradant dimers of dimethyl fumarate. See Griffin et al., U.S. Pat. No. 3,139,395; and Griffin et al., "The chemistry of photodimers of maleic and fumaric acid derivatives. I. Dimethyl fumarate dimer," *J Am Chem Soc* (1961), 83: 2725-2728. For example, compound (1) can theoretically exist in four different isomeric forms, though one of the four isomers is formed in preference to the other forms, the preferred isomeric form being the "chair" form of compound IVa shown in Griffin et al., *J Am Chem Soc*, supra. Thus, in some embodiments, the one or more compounds of Formula (I) include the "chair" form isomers of Formula (I).

The toxicity of compound (1) was evaluated using Derek Nexus version 2.0 (Lhasa Ltd., Leeds, UK) which predicts toxicity based on a combination of published reports as well as compound structural characteristics and provides one of seven possible grades for toxicity. The Derek Nexus database provides no toxicity rating for compound (1), meaning that the compound would be considered by the pharmaceutical industry and the US FDA as not being potentially genotoxic. Although not considered toxic/genotoxic, the presence of compound (1) is undesirable from the standpoint that the pharmacologically active agent, DMF, is degrading into a material that is not pharmacologically active, and so the strength and potency of the pharmaceutical composition and/or dosage form is changing over time as the DMF degrades.

Figure 2:
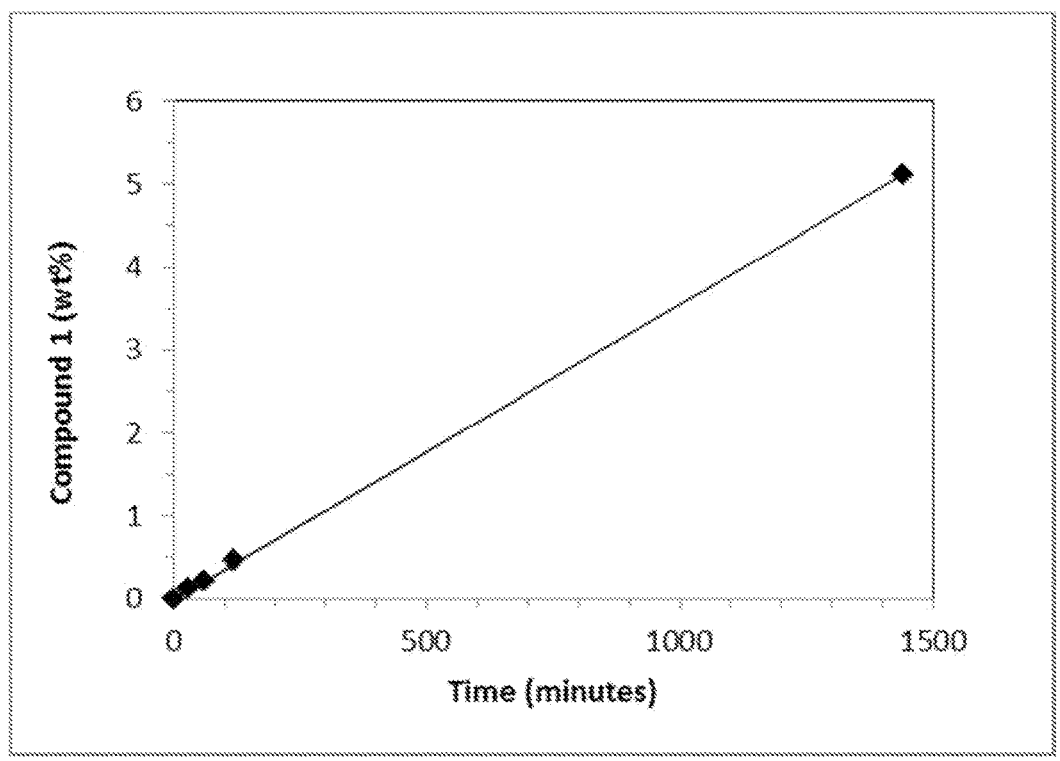
FIG. 2 shows the formation of compound (1) after DMF powder has been exposed to fluorescent light for 24 hours.

Compounds of Formula (I), including specifically compound (1) and its NMR spectrum are shown in FIG. 2 of Lai et al. US 2008/0033199, the disclosure of which is incorporated herein by reference. Using well established analytical chemistry techniques in combination with the disclosures in the Lai et al. publication, those skilled in the art can test pharmaceutical compositions and dosage forms for the presence of compounds of Formula (I). Stability testing for the presence of photolabile drug degradants such as compounds of Formula (I) can also be performed in accordance with the International Conference on Harmonisation of Technical Requirements for Registration of Pharmaceuticals for Human Use (ICH) Guideline Q1B, 1997a, Photostability testing of new drug substances and products, Federal Register, 62, 27115-27122.

In order to maintain a low content of photodegradant compounds of Formula (I) in a DMF-containing pharmaceutical composition or dosage form, the DMF active pharmaceutical ingredient as well as the dosage form should both be manufactured with minimal exposure to visible and/or UV light. When pure DMF powder is exposed to $17.7 \times 10^3$ lux·hr of fluorescent light, about 0.2 wt % of compound (1) is formed; and when exposed to $8.8 \times 10^3$ lux·hr of fluorescent light, about 0.1 wt % of compound (1) is formed. See Example 1 herein. When pure DMF powder is exposed to 11.2 watt·hr/m² of near-UV light, about 0.2 wt % of compound (1) is formed; and when exposed to 5.6 watt·hr/m² of near-UV light, about 0.1 wt % of compound (1) is formed. See Example 2 herein. Thus, DMF powder should be exposed to visible and UV light levels below these limits in order to maintain the levels of photodegradant compounds of Formula (I) within acceptable ranges.

In order to reduce the impact of light, including natural light, ultra-violet light and near-UV light, on the stability of DMF in a DMF-containing dosage form, a barrier layer or coating can be applied to the dosage form. For oral dosage forms, examples include a coating on a DMF-containing tablet or an opaque capsule containing DMF particles or pellets.

In some embodiments, the tablet or capsule coating is opaque and has a thickness of at least 10 μm. In some embodiments, the coating has a thickness of at least 300 μm. The coating may comprise a filler and/or a polymer. The coating may comprise an iron oxide colorant and other excipients. Alternatively, the coating may comprise a colorant (e.g., FD&C Yellow #6, Sunset Yellow, or FD&C Red #40 Allura Red) and other known coating excipients. Alternatively, the coating may comprise titanium dioxide, silicon dioxide or zinc dioxide and other known coating excipients.

The use of opaque plastic (e.g., high density polyethylene) pill bottles, e.g., with child-resistant screw caps, is one option to limit the amount of light exposure to a DMF-containing dosage form. Blister packs, a term used for several types of pre-formed plastic pharmaceutical packaging, is another option. The primary component of a blister pack is a cavity or pocket made from a formable web, usually a thermoformed plastic. This usually has a backing of paperboard or a lidding seal of aluminum foil or plastic. The plastics can be made opaque, and/or with an anti-UV light coating, to limit the amount of light exposure to the DMF dosage form.

In a second aspect, a pharmaceutical composition is provided which comprises (a) dimethyl fumarate in solid form; and (b) one or more succinate compounds of Formula (II):

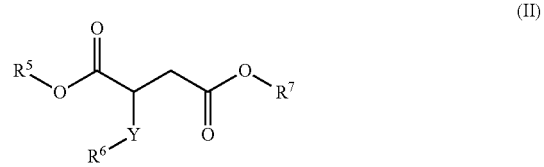

isomers thereof, and salts of any of the foregoing, wherein:
each of $R^5$ and $R^7$ is independently chosen from hydrogen and methyl;
Y is chosen from O, S, NH and $NR^8$;
$R^6$ is chosen from hydrogen, lower alkyl and aryl; and
$R^8$ is chosen from lower alkyl.

In some embodiments, the dimethyl fumarate is in crystalline form. In some embodiments, the dimethyl fumarate is in amorphous form.

In some embodiments, each of $R^6$ and $R^8$ is independently unsubstituted alkyl. In some embodiments, each of $R^6$ and $R^8$ is independently alkyl, substituted with hydroxy.

In some embodiments, the one or more compounds of Formula (II) are present in a total combined amount of less than 3 wt % based on the total weight of the dimethyl fumarate.

In some embodiments, the one or more compounds of Formula (II) are present in a total combined amount of less than 2 wt % based on the total weight of the dimethyl fumarate.

In some embodiments, the one or more compounds of Formula (II) are present in a total combined amount of less than 1 wt % based on the total weight of the dimethyl fumarate.

In some embodiments, the one or more compounds of Formula (II) are present in a combined total amount of less than about 3% by weight based on the total weight of the dimethyl fumarate. In some embodiments, the one or more compounds of Formula (II) are present in a combined total amount of less than about 2% by weight based on the total weight of the dimethyl fumarate. In some embodiments, the one or more compounds of Formula (II) are present in a combined total amount of less than about 1.8% by weight based on the total weight of the dimethyl fumarate. In some embodiments, the one or more compounds of Formula (II) are present in a combined total amount of less than about 1.6% by weight based on the total weight of the dimethyl fumarate. In some embodiments, the one or more compounds of Formula (II) are present in a combined total amount of less than about 1.4% by weight based on the total weight of the dimethyl fumarate. In some embodiments, the one or more compounds) of Formula (II) are present in a combined total amount of less than about 1.2% by weight based on the total weight of the dimethyl fumarate. In some embodiments, the one or more compounds of Formula (II) are present in a combined total amount of less than about 1.0% by weight based on the total weight of the dimethyl fumarate. In some embodiments, the one or more compounds of Formula (II) are present in a combined total amount of less than about 0.8% by weight based on the total weight of the dimethyl fumarate. In some embodiments, the one or more compounds of Formula (II) are present in a combined total amount of less than about 0.6% by weight based on the total weight of the dimethyl fumarate. In some embodiments, the one or more compounds of Formula (II) are present in a combined total amount of less than about 0.4% by weight based on the total weight of the dimethyl fumarate. In some embodiments, the one or more compounds of Formula (II) are present in a combined total amount of less than about 0.2% by weight based on the total weight of the dimethyl fumarate. In some embodiments, the one or more compounds of Formula (II) are present in a combined total amount of less than about 0.1% by weight based on the total weight of the dimethyl fumarate.

In some embodiments, the one or more compounds of Formula (II) are present in a combined total amount of about 0.001% to 3% by weight based on the total weight of the dimethyl fumarate. In some embodiments, the one or more compounds of Formula (II) are present in a combined total amount of about 0.001% to 2% by weight based on the total weight of the dimethyl fumarate. In some embodiments, the one or more compounds of Formula (II) are present in a combined total amount of about 0.001% to 1.8% by weight based on the total weight of the dimethyl fumarate. In some embodiments, the one or more compounds of Formula (II) are present in a combined total amount of about 0.001% to 1.6% by weight based on the total weight of the dimethyl fumarate. In some embodiments, the one or more compounds of Formula (II) are present in a combined total amount of about 0.001% to 1.4% by weight based on the total weight of the dimethyl fumarate. In some embodiments, the one or more compounds of Formula (II) are present in a combined total amount of about 0.001% to 1.2% by weight based on the total weight of the dimethyl fumarate. In some embodiments, the one or more compounds of Formula (II) are present in a combined total amount of about 0.001% to 1.0% by weight based on the total weight of the dimethyl fumarate. In some embodiments, the one or more compounds of Formula (II) are present in a combined total amount of about 0.001% to 0.8% by weight based on the total weight of the dimethyl fumarate. In some embodiments, the one or more compounds of Formula (II) are present in a combined total amount of about 0.001% to 0.6% by weight based on the total weight of the dimethyl fumarate. In some embodiments, the one or more compounds of Formula (II) are present in a combined total amount of about 0.001% to 0.4% by weight based on the total weight of the dimethyl fumarate. In some embodiments, the one or more compounds of Formula (II) are present in a combined total amount of about 0.001% to 0.2% by weight based on the total weight of the dimethyl fumarate. In some embodiments, the one or more compounds of Formula (II) are present in a combined total amount of about 0.001% to 0.1% by weight based on the total weight of the dimethyl fumarate.

Compounds of Formula (II) include the following: dimethyl 2-hydroxysuccinate; 2-hydroxy-4-methoxy-4-oxobutanoic acid; 3-hydroxy-4-methoxy-4-oxobutanoic acid; 2-hydroxysuccinic acid; dimethyl 2-mercaptosuccinate; 2-mercapto-4-methoxy-4-oxobutanoic acid; 3-mercapto-4-methoxy-4-oxobutanoic acid; 2-mercaptosuccinic acid; dimethyl 2-aminosuccinate; 2-amino-4-methoxy-4-oxobutanoic acid; 3-amino-4-methoxy-4-oxobutanoic acid; 2-aminosuccinic acid; as well as isomers thereof, and salts of any of the foregoing.

In some embodiments, each of the one or more compounds of Formula (II) is present in an amount of less than about 0.2% by weight based on the total weight of the dimethyl fumarate. In some embodiments, each of the one or more compounds of Formula (II) is present in an amount of less than about 0.15% by weight based on the total weight of the dimethyl fumarate. In some embodiments, each of the one or more compounds of Formula (II) is present in an amount of less than about 0.1% by weight based on the total weight of the dimethyl fumarate. In some embodiments, each of the one or more compounds of Formula (II) is present in an amount of less than about 0.05% by weight based on the total weight of the dimethyl fumarate.

In some embodiments, each of the one or more compounds of Formula (II) is present in an amount of about 0.001% to 0.2% by weight based on the total weight of the dimethyl fumarate. In some embodiments, each of the one or more compounds of Formula (II) is present in an amount of about 0.001% to 0.15% by weight based on the total weight of the dimethyl fumarate. In some embodiments, each of the one or more compounds of Formula (II) is present in an amount of about 0.001% to 0.1% by weight based on the total weight of the dimethyl fumarate. In some embodiments, each of the one or more compounds of Formula (II) is present in an amount of about 0.001% to 0.05% by weight based on the total weight of the dimethyl fumarate.

In another aspect, the DMF-containing pharmaceutical compositions and dosage forms disclosed herein contain little or no alkanols or alcohols, thioalkanols or alkyl mercaptans, alkylamines, dialkylamines or any compound capable of acting as a nucleophile for addition to the double bond of DMF. For example, use of alcohols in a pharmaceutical composition can form the 2-alkoxy compound (Formula II, —Y—$R^6$ is —O-alkyl) impurities into the formulation. Similarly, use of thioalcohols or mercaptans in a pharmaceutical composition can form the 2-thioalkoxy compound (Formula II, —Y—$R^6$ is —S-alkyl) impurities into the formulation. Furthermore, use of primary amines in a pharmaceutical composition can form the 2-alkylamino compound (Formula II, —Y—$R^6$ is —NH-alkyl) impurities into the formulation. Moreover, use of secondary amines in a pharmaceutical composition can form the 2-dialkylamino compound (Formula II, —Y—$R^6$ is —N(alkyl)$_2$) impurities into the formulation.

Thus in some embodiments, the pharmaceutical compositions and dosage forms disclosed herein are substantially free of any alcohols, mercaptans, alkylamines, or dialkylamines. In some embodiments, the pharmaceutical compositions and dosage forms disclosed herein are substantially free of methanol, ethanol, methyl mercaptan, ethylamine, propylamine, butylamine, aspartame, diethanolamine, meglumine, monoethanolamine, or triethanolamine.

In a third aspect, a pharmaceutical composition is provided which comprises (a) dimethyl fumarate in solid form; and (b) an oxirane compound of Formula (III):

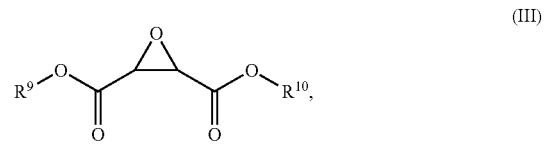

(III)

isomers thereof, and salts of any of the foregoing, wherein:

each of $R^9$ and $R^{10}$ is independently chosen from hydrogen and methyl; and wherein the one or more compounds of Formula (III) are each present in an amount of less than 15 ppm based on the total weight of the dimethyl fumarate.

In a third aspect, a dosage form for treating multiple sclerosis is provided which comprises (a) dimethyl fumarate in solid form; and (b) an oxirane compound of Formula (III):

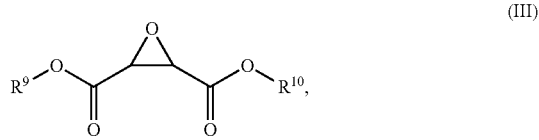

(III)

isomers thereof, and salts of any of the foregoing, wherein:

each of $R^9$ and $R^{10}$ is independently chosen from hydrogen and methyl; and wherein the one or more compounds of Formula (III) are each present in an amount of less than 15 ppm based on the total weight of the dimethyl fumarate.

In some embodiments of the pharmaceutical compositions and/or dosage forms, the dimethyl fumarate is crystalline. In some embodiments of the pharmaceutical compositions and/or dosage forms, the dimethyl fumarate is amorphous.

In some embodiments of the pharmaceutical compositions and/or dosage forms, the one or more compounds of Formula (III) are present in a total combined amount of less than about 15 ppm based on the total weight of the dimethyl fumarate. In some embodiments of the pharmaceutical compositions and/or dosage forms, the one or more compounds of Formula (III) are present in a total combined amount of less than about 12 ppm based on the total weight of the dimethyl fumarate. In some embodiments of the pharmaceutical compositions and/or dosage forms, the one or more compounds of Formula (III) are present in a total combined amount of less than about 10 ppm based on the total weight of the dimethyl fumarate. In some embodiments of the pharmaceutical compositions and/or dosage forms, the one or more compounds of Formula (III) are present in a total combined amount of less than about 8 ppm based on the total weight of the dimethyl fumarate. In some embodiments of the pharmaceutical compositions and/or dosage forms, the one or more compounds of Formula (III) are present in a total combined amount of less than about 5 ppm based on the total weight of the dimethyl fumarate. In some embodiments of the pharmaceutical compositions and/or dosage forms, the one or more compounds of Formula (III) are present in a total combined amount of less than about 4.5 ppm based on the total weight of the dimethyl fumarate. In some embodiments of the pharmaceutical compositions and/or dosage forms, the one or more compounds of Formula (III) are present in a total combined amount of less than about 4 ppm based on the total weight of the dimethyl fumarate. In some embodiments of the pharmaceutical compositions and/or dosage forms, the one or more compounds of Formula (III) are present in a total combined amount of less than about 3.5 ppm based on the total weight of the dimethyl fumarate. In some embodiments of the pharmaceutical compositions and/or dosage forms, the one or more compounds of Formula (III) are present in a total combined amount of less than about 3 ppm based on the total weight of the dimethyl fumarate. In some embodiments of the pharmaceutical compositions and/or dosage forms, the one or more compounds of Formula (III) are present in a total combined amount of less than about 2.5 ppm based on the total weight of the dimethyl fumarate. In some embodiments of the pharmaceutical compositions and/or dosage forms, the one or more compounds of Formula (III) are present in a total combined amount of less than about 2 ppm based on the total weight of the dimethyl fumarate. In some embodiments of the pharmaceutical compositions and/or dosage forms, the one or more compounds of Formula (III) are present in a total combined amount of less than about 1.5 ppm based on the total weight of the dimethyl fumarate. In some embodiments of the pharmaceutical compositions and/or dosage forms, the one or more compounds of Formula (III) are present in a total combined amount of less than about 1 ppm based on the total weight of the dimethyl fumarate. In some embodiments of the pharmaceutical compositions and/or dosage forms, the one or more compounds of Formula (III) are present in a total combined amount of less than about 0.5 ppm based on the total weight of the dimethyl fumarate.

In some embodiments of the pharmaceutical compositions and/or dosage forms, the one or more compounds of Formula (III) are present in a total combined amount of less than about 0.1 ppm to 15 ppm based on the total weight of the dimethyl fumarate. In some embodiments of the pharmaceutical compositions and/or dosage forms, the one or more compounds of Formula (III) are present in a total combined amount of less than about 0.1 ppm to 12 ppm based on the total weight of the dimethyl fumarate. In some embodiments of the pharmaceutical compositions and/or dosage forms, the one or more compounds of Formula (III) are present in a total combined amount of less than about 0.1 ppm to 10 ppm based on the total weight of the dimethyl fumarate. In some embodiments of the pharmaceutical compositions and/or dosage forms, the one or more compounds of Formula (III) are present in a total combined amount of less than about 0.1 ppm to 8 ppm based on the total weight of the dimethyl fumarate. In some embodiments of the pharmaceutical compositions and/or dosage forms, the one or more compounds of Formula (III) are present in a total combined amount of less than about 0.1 ppm to 5 ppm based on the total weight of the dimethyl fumarate. In some embodiments of the pharmaceutical compositions and/or dosage forms, the one or more compounds of Formula (III) are present in a total combined amount of about 0.1 ppm to 4.5 ppm based on the total weight of the dimethyl fumarate. In some embodiments of the pharmaceutical compositions and/or dosage forms, the one or more compounds of Formula (III) are present in a total combined amount of about 0.1 ppm to 4 ppm based on the total weight of the dimethyl fumarate. In some embodiments of the pharmaceutical compositions and/or dosage forms, the one or more compounds of Formula (III) are present in a total combined amount of about 0.1 ppm to 3.5 ppm based on the total weight of the dimethyl fumarate. In some embodiments of the pharmaceutical compositions and/or dosage forms, the one or more compounds of Formula (III) are present in a total combined amount of about 0.1 ppm to 3 ppm based on the total weight of the dimethyl fumarate. In some embodiments of the pharmaceutical compositions and/or dosage forms, the one or more compounds of Formula (III) are present in a total combined amount of about 0.1 ppm to 2.5 ppm based on the total weight of the dimethyl fumarate. In some embodiments of the pharmaceutical compositions and/or dosage forms, the one or more compounds of Formula (III) are present in a total combined amount of about 0.1 ppm to 2 ppm based on the total weight of the dimethyl fumarate. In some embodiments of the pharmaceutical compositions and/or dosage forms, the one or more compounds of Formula (III) are present in a total combined amount of about 0.1 ppm to 1.5 ppm based on the total weight of the dimethyl fumarate. In some embodiments of the pharmaceutical compositions and/or dosage forms, the one or more compounds of Formula (III) are present in a total combined amount of about 0.1 ppm to 1 ppm based on the total weight of the dimethyl fumarate. In some embodiments of the pharmaceutical compositions and/or dosage forms, the one or more compounds of Formula (III) are present in a total combined amount of about 0.1 ppm to 0.5 ppm based on the total weight of the dimethyl fumarate.

In some embodiments of the pharmaceutical compositions and/or dosage forms, the one or more compounds of Formula (III) include the following: dimethyl oxirane-2,3-dicarboxylate (compound (2)), in which both $R^9$ and $R^{10}$ are methyl; 3-(methoxycarbonyl)oxirane-2-carboxylic acid, in which $R^9$ is methyl and $R^{10}$ is hydrogen; oxirane-2,3-dicarboxylic acid, in which both $R^9$ and $R^{10}$ are hydrogen; isomers thereof, and salts of any of the foregoing In some embodiments of the pharmaceutical compositions and/or dosage forms, the one or more compounds of Formula (III) comprise dimethyl oxirane-2,3-dicarboxylate, isomers thereof, and salts of any of the foregoing. In some embodiments of the pharmaceutical compositions and/or dosage forms, the one or more compounds of Formula (III) comprise dimethyl oxirane-2,3-dicarboxylate.

In some embodiments of the pharmaceutical compositions and/or dosage forms, each of the one or more compounds of Formula (III) is present in an amount of less than about 15 ppm based on the total weight of the dimethyl fumarate. In some embodiments of the pharmaceutical compositions and/or dosage forms, each of the one or more compounds of Formula (III) is present in an amount of less than about 12 ppm based on the total weight of the dimethyl fumarate. In some embodiments of the pharmaceutical compositions and/or dosage forms, each of the one or more compounds of Formula (III) is present in an amount of less than about 10 ppm based on the total weight of the dimethyl fumarate. In some embodiments of the pharmaceutical compositions and/or dosage forms, each of the one or more compounds of Formula (III) is present in an amount of less than about 8 ppm based on the total weight of the dimethyl fumarate. In some embodiments of the pharmaceutical compositions and/or dosage forms, each of the one or more compounds of Formula (III) is present in an amount of less than about 5 ppm based on the total weight of the dimethyl fumarate. In some embodiments of the pharmaceutical compositions and/or dosage forms, each of the one or more compounds of Formula (III) is present in an amount of less than about 3 ppm based on the total weight of the dimethyl fumarate. In some embodiments of the pharmaceutical compositions and/or dosage forms, each of the one or more compounds of Formula (III) is present in an amount of less than about 2 ppm based on the total weight of the dimethyl fumarate. In some embodiments of the pharmaceutical compositions and/or dosage forms, each of the one or more compounds of Formula (III) is present in an amount of less than about 1 ppm based on the total weight of the dimethyl fumarate.

In some embodiments of the pharmaceutical compositions and/or dosage forms, each of the one or more compounds of Formula (III) is present in an amount of about 0.1 ppm to about 15 ppm based on the total weight of the dimethyl fumarate. In some embodiments of the pharmaceutical compositions and/or dosage forms, each of the one or more compounds of Formula (III) is present in an amount of about 0.1 ppm to about 12 ppm based on the total weight of the dimethyl fumarate. In some embodiments of the pharmaceutical compositions and/or dosage forms, each of the one or more compounds of Formula (III) is present in an amount of about 0.1 ppm to about 10 ppm based on the total weight of the dimethyl fumarate. In some embodiments of the pharmaceutical compositions and/or dosage forms, each of the one or more compounds of Formula (III) is present in an amount of about 0.1 ppm to about 8 ppm based on the total weight of the dimethyl fumarate. In some embodiments of the pharmaceutical compositions and/or dosage forms, each of the one or more compounds of Formula (III) is present in an amount of about 0.1 ppm to about 5 ppm based on the total weight of the dimethyl fumarate. In some embodiments of the pharmaceutical compositions and/or dosage forms, each of the one or more compounds of Formula (III) is present in an amount of about 0.1 ppm to about 3 ppm based on the total weight of the dimethyl fumarate. In some embodiments of the pharmaceutical compositions and/or dosage forms, each of the one or more compounds of Formula (III) is present in an amount of about 0.1 ppm to about 2 ppm based on the total weight of the dimethyl fumarate. In some embodiments of the pharmaceutical compositions and/or dosage forms, each of the one or more compounds of Formula (III) is present in an amount of about 0.1 ppm to about 1 ppm based on the total weight of the dimethyl fumarate.

The toxicity of dimethyl oxirane-2,3-dicarboxylate (compound (2)) was evaluated using Derek Nexus version 2.0 (Lhasa Ltd., Leeds, UK) which predicts toxicity based on a combination of published reports as well as compound structural characteristics and provides one of seven possible grades for toxicity: certain, probable, plausible, equivocal, doubted, improbable and impossible. Although there are no published reports testing the toxicity of compound (2), due to the epoxide portion of the molecule, the Derek Nexus database rates the toxicity of compound (2) as "plausible" meaning that the weight of evidence supports the proposition that the compound is toxic.

Compound (2) and its NMR spectrum are shown in Example 1 of Habich et al. U.S. Pat. No. 4,863,916, the disclosures of which are incorporated herein by reference. Using established analytical chemistry techniques, together with the disclosures in the Habich et al. patent, those skilled in the art can test pharmaceutical compositions and dosage forms for the presence of compound (2).

In another aspect, the DMF-containing pharmaceutical compositions and dosage forms disclosed herein contain little or no polyvinylpyrrolidone (PVP) or polyethylene glycol (PEG). Use of polyvinylpyrrolidone (PVP) in a pharmaceutical composition can introduce peroxide impurities into the formulation since the PVP polymerization process involves the use of polymerization initiators such as peroxides, ozone, and hydrogen peroxides. Upon heat or light exposure, even trace amounts of peroxides can decompose into free radicals, which can powerfully catalyze photochemical reactions. Light-induced decomposition of polyoxyethylene chains of polyethylene glycols (PEG) or polysorbate surfactants can also result in the formation of hydrogen peroxides and/or peroxide-free radicals, which can promote degradation of DMF.

Thus in some embodiments, the pharmaceutical compositions and dosage forms disclosed herein are substantially free of any polyvinylpyrrolidone, polyethylene glycol and/or polysorbate surfactant. In some embodiments, the pharmaceutical compositions and dosage forms disclosed herein contain no polyvinylpyrrolidone, polyethylene glycol and/or polysorbate surfactant.

In another aspect, the DMF-containing pharmaceutical compositions and dosage forms disclosed herein may comprise an antioxidant. Suitable antioxidants include methyl paraben and propyl paraben and their salts (such as sodium, potassium), vitamin E, vitamin E TPGS, propyl gallate, sulfites, ascorbic acid, sodium benzoate, citric acid, cyclodextrins, peroxide scavengers, benzoic acid, ethylenediaminetetraacetic acid (EDTA) and salts thereof, chain terminators (e.g., thiols and phenols), butylated hydroxytoluene (BHT), butylated hydroxyanisole (BHA) and the like, and combinations of any of the foregoing. In some embodiments, antioxidants such as butylated hydroxytoluene (BHT) and butylated hydroxyanisole (BHA) can be used. In some embodiments, the antioxidant may be present in an amount of about from 0.01 to 5.0%, and in some embodiments about from 0.5 to 2.0% by weight of the total pharmaceutical composition.

In another aspect, the DMF-containing pharmaceutical compositions and dosage forms disclosed herein may comprise an antioxidant. Suitable free radical scavengers include tocopherol, naringenin and the like, and mixtures thereof.

In another aspect, DMF-containing pharmaceutical compositions and dosage forms comprise one or more vehicles or other excipients that are low in oxidizing agents such as hydrogen peroxide, formaldehydes and formic acid and low in metallic impurities such as iron ions (e.g., $Fe^{+2}$) that have the capability to oxidize DMF, leading to the formation of compound (2).

In a fourth aspect, a pharmaceutical composition is provided which comprises (a) dimethyl fumarate in solid form; and (b) one or more succinate compounds of Formula (IV):

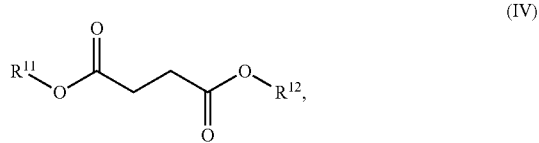

(IV)

isomers thereof, and salts of any of the foregoing, wherein:

each of $R^{11}$ and $R^{12}$ is independently chosen from hydrogen and methyl.

In some embodiments, the dimethyl fumarate is in crystalline form. In some embodiments, the dimethyl fumarate is in amorphous form.

In some embodiments, the one or more compounds of Formula (IV) are present in a total combined amount of less than 2 wt % based on the total weight of the dimethyl fumarate.

In some embodiments, the one or more compounds of Formula (IV) are present in a total combined amount of less than 1 wt % based on the total weight of the dimethyl fumarate.

In some embodiments, the one or more compounds of Formula (IV) are present in a combined total amount of less than about 2% by weight based on the total weight of the dimethyl fumarate. In some embodiments, the one or more compounds of Formula (IV) are present in a combined total amount of less than about 1.8% by weight based on the total weight of the dimethyl fumarate. In some embodiments, the one or more compounds of Formula (IV) are present in a combined total amount of less than about 1.6% by weight based on the total weight of the dimethyl fumarate. In some embodiments, the one or more compounds of Formula (IV) are present in a combined total amount of less than about 1.4% by weight based on the total weight of the dimethyl fumarate. In some embodiments, the one or more compounds of Formula (IV) are present in a combined total amount of less than about 1.2% by weight based on the total weight of the dimethyl fumarate. In some embodiments, the one or more compounds of Formula (IV) are present in a combined total amount of less than about 1.0% by weight based on the total weight of the dimethyl fumarate. In some embodiments, the one or more compounds of Formula (IV) are present in a combined total amount of less than about 0.8% by weight based on the total weight of the dimethyl fumarate. In some embodiments, the one or more compounds of Formula (IV) are present in a combined total amount of less than about 0.6% by weight based on the total weight of the dimethyl fumarate. In some embodiments, the one or more compounds of Formula (IV) are present in a combined total amount of less than about 0.4% by weight based on the total weight of the dimethyl fumarate. In some embodiments, the one or more compounds of Formula (IV) are present in a combined total amount of less than about 0.2% by weight based on the total weight of the dimethyl fumarate. In some embodiments, the one or more compounds of Formula (IV) are present in a combined total amount of less than about 0.1% by weight based on the total weight of the dimethyl fumarate.

In some embodiments, the one or more compounds of Formula (IV) are present in a combined total amount of about 0.001% to 2% by weight based on the total weight of the dimethyl fumarate. In some embodiments, the one or more compounds of Formula (IV) are present in a combined total amount of about 0.001% to 1.8% by weight based on the total weight of the dimethyl fumarate. In some embodiments, the one or more compounds of Formula (IV) are present in a combined total amount of about 0.001% to 1.6% by weight based on the total weight of the dimethyl fumarate. In some embodiments, the one or more compounds of Formula (IV) are present in a combined total amount of about 0.001% to 1.4% by weight based on the total weight of the dimethyl fumarate. In some embodiments, the one or more compounds of Formula (IV) are present in a combined total amount of about 0.001% to 1.2% by weight based on the total weight of the dimethyl fumarate. In some embodiments, the one or more compounds of Formula (IV) are present in a combined total amount of about 0.001% to 1.0% by weight based on the total weight of the dimethyl fumarate. In some embodiments, the one or more compounds of Formula (IV) are present in a combined total amount of about 0.001% to 0.8% by weight based on the total weight of the dimethyl fumarate. In some embodiments, the one or more compounds of Formula (IV) are present in a combined total amount of about 0.001% to 0.6% by weight based on the total weight of the dimethyl fumarate. In some embodiments, the one or more compounds of Formula (IV) are present in a combined total amount of about 0.001% to 0.4% by weight based on the total weight of the dimethyl fumarate. In some embodiments, the one or more compounds of Formula (IV) are present in a combined total amount of about 0.001% to 0.2% by weight based on the total weight of the dimethyl fumarate. In some embodiments, the one or more compounds of Formula (IV) are present in a combined total amount of about 0.001% to 0.1% by weight based on the total weight of the dimethyl fumarate.

Compounds of Formula (IV) include the following: dimethyl succinate in which both $R^{11}$ and $R^{12}$ are methyl; 4-methoxy-4-oxobutanoic acid in which $R^{11}$ is methyl and $R^{12}$ is hydrogen; succinic acid in which both $R^{11}$ and $R^{12}$ are hydrogen; and isomers thereof, and salts of any of the foregoing.

In some embodiments, each of the one or more compounds of Formula (IV) is present in an amount of less than about 0.2% by weight based on the total weight of the dimethyl fumarate. In some embodiments, each of the one or more compounds of Formula (IV) is present in an amount of less than about 0.2% by weight based on the total weight of the dimethyl fumarate. In some embodiments, each of the one or more compounds of Formula (IV) is present in an amount of less than about 0.15% by weight based on the total weight of the dimethyl fumarate. In some embodiments, each of the one or more compounds of Formula (IV) is present in an amount of less than about 0.1% by weight based on the total weight of the dimethyl fumarate. In some embodiments, each of the one or more compounds of Formula (IV) is present in an amount of less than about 0.05% by weight based on the total weight of the dimethyl fumarate.

In some embodiments, each of the one or more compounds of Formula (IV) is present in an amount of about 0.001% to 0.3% by weight based on the total weight of the dimethyl fumarate. In some embodiments, each of the one or more compounds of Formula (IV) is present in an amount of about 0.001% to 0.2% by weight based on the total weight of the dimethyl fumarate. In some embodiments, each of the one or more compounds of Formula (IV) is present in an amount of about 0.001% to 0.15% by weight based on the total weight of the dimethyl fumarate. In some embodiments, each of the one or more compounds of Formula (IV) is present in an amount of about 0.001% to 0.1% by weight based on the total weight of the dimethyl fumarate. In some embodiments, each of the one or more compound of Formula (IV) is present in an amount of about 0.001% to 0.05% by weight based on the total weight of the dimethyl fumarate.

In another aspect, the DMF-containing pharmaceutical compositions and dosage forms disclosed herein contain little or no compound(s) capable of forming hydrogen or hydrogen radicals which will, in turn, facilitate the reduction of the double bond of DMF.

Thus in some embodiments, the pharmaceutical compositions and dosage forms disclosed herein are substantially free of any compounds containing hydrazino group.

In a fifth aspect, a pharmaceutical composition is provided which comprises (a) dimethyl fumarate in solid form; and (b) one or more succinate compounds of Formula (V):

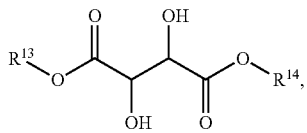

(V)

isomers thereof, and salts of any of the foregoing wherein:
each of $R^{13}$ and $R^{14}$ is independently chosen from hydrogen and methyl.

In some embodiments, the dimethyl fumarate is in crystalline form. In some embodiments, the dimethyl fumarate is in amorphous form.

In some embodiments, the one or more compounds of Formula (V) are present in a total combined amount of less than 2 wt % based on the total weight of the dimethyl fumarate.

In some embodiments, the one or more compounds of Formula (V) are present in a total combined amount of less than 1 wt % based on the total weight of the dimethyl fumarate.

In some embodiments, the one or more compounds of Formula (V) are present in a combined total amount of less than about 2% by weight based on the total weight of the dimethyl fumarate. In some embodiments, the one or more compounds of Formula (V) are present in a combined total amount of less than about 1.8% by weight based on the total weight of the dimethyl fumarate. In some embodiments, the one or more compounds of Formula (V) are present in a combined total amount of less than about 1.6% by weight based on the total weight of the dimethyl fumarate. In some embodiments, the one or more compounds of Formula (V) are present in a combined total amount of less than about 1.4% by weight based on the total weight of the dimethyl fumarate. In some embodiments, the one or more compounds of Formula (V) are present in a combined total amount of less than about 1.2% by weight based on the total weight of the dimethyl fumarate. In some embodiments, the one or more compounds of Formula (V) are present in a combined total amount of less than about 1.0% by weight based on the total weight of the dimethyl fumarate. In some embodiments, the one or more compounds of Formula (V) are present in a combined total amount of less than about 0.8% by weight based on the total weight of the dimethyl fumarate. In some embodiments, the one or more compounds of Formula (V) are present in a combined total amount of less than about 0.6% by weight based on the total weight of the dimethyl fumarate. In some embodiments, the one or more compounds of Formula (V) are present in a combined total amount of less than about 0.4% by weight based on the total weight of the dimethyl fumarate. In some embodiments, the one or more compounds of Formula (V) are present in a combined total amount of less than about 0.2% by weight based on the total weight of the dimethyl fumarate. In some embodiments, the one or more compounds of Formula (V) are present in a combined total amount of less than about 0.1% by weight based on the total weight of the dimethyl fumarate.

In some embodiments, the one or more compounds of Formula (V) are present in a combined total amount of about 0.001% to 2% by weight based on the total weight of the dimethyl fumarate. In some embodiments, the one or more compounds of Formula (V) are present in a combined total amount of about 0.001% to 1.8% by weight based on the total weight of the dimethyl fumarate. In some embodiments, the one or more compounds of Formula (V) are present in a combined total amount of about 0.001% to 1.6% by weight based on the total weight of the dimethyl fumarate. In some embodiments, the one or more compounds of Formula (V) are present in a combined total amount of about 0.001% to 1.4% by weight based on the total weight of the dimethyl fumarate. In some embodiments, the one or more compounds of Formula (V) are present in a combined total amount of about 0.001% to 1.2% by weight based on the total weight of the dimethyl fumarate. In some embodiments, the one or more compounds of Formula (V) are present in a combined total amount of about 0.001% to 1.0% by weight based on the total weight of the dimethyl fumarate. In some embodiments, the one or more compounds of Formula (V) are present in a combined total amount of about 0.001% to 0.8% by weight based on the total weight of the dimethyl fumarate. In some embodiments, the one or more compounds of Formula (V) are present in a combined total amount of about 0.001% to 0.6% by weight based on the total weight of the dimethyl fumarate. In some embodiments, the one or more compounds of Formula (V) are present in a combined total amount of about 0.001% to 0.4% by weight based on the total weight of the dimethyl fumarate. In some embodiments, the one or more compounds of Formula (V) are present in a combined total amount of about 0.001% to 0.2% by weight based on the total weight of the dimethyl fumarate. In some embodiments, the one or more compounds of Formula (V) are present in a combined total amount of about 0.001% to 0.1% by weight based on the total weight of the dimethyl fumarate.

Compounds of Formula (V) include the following: 2,3-dihydroxysuccinic acid dimethyl ester, in which both $R^{13}$ and R[14] are methyl; 2,3-dihydroxysuccinic acid monomethyl ester, in which R[13] is methyl and R[14] is hydrogen; 2,3-dihydroxysuccinic acid, in which both R[13] and R[14] are hydrogen; and isomers thereof, and salts of any of the foregoing.

In some embodiments, each of the one or more compounds of Formula (V) is present in an amount of less than about 0.3% by weight based on the total weight of the dimethyl fumarate. In some embodiments, each of the one or more compounds of Formula (V) is present in an amount of less than about 0.2% by weight based on the total weight of the dimethyl fumarate. In some embodiments, each of the one or more compounds of Formula (V) is present in an amount of less than about 0.15% by weight based on the total weight of the dimethyl fumarate. In some embodiments, each of the one or more compounds of Formula (V) is present in an amount of less than about 0.1% by weight based on the total weight of the dimethyl fumarate. In some embodiments, each of the one or more compounds of Formula (V) is present in an amount of less than about 0.05% by weight based on the total weight of the dimethyl fumarate.

In some embodiments, each of the one or more compounds of Formula (V) is present in an amount of about 0.001% to 0.3% by weight based on the total weight of the dimethyl fumarate. In some embodiments, each of the one or more compounds of Formula (V) is present in an amount of about 0.001% to 0.2% by weight based on the total weight of the dimethyl fumarate. In some embodiments, each of the one or more compounds of Formula (V) is present in an amount of about 0.001% to 0.15% by weight based on the total weight of the dimethyl fumarate. In some embodiments, each of the one or more compounds of Formula (V) is present in an amount of about 0.001% to 0.1% by weight based on the total weight of the dimethyl fumarate. In some embodiments, each of the one or more compounds of Formula (V) is present in an amount of about 0.001% to 0.05% by weight based on the total weight of the dimethyl fumarate.

In another aspect, the DMF-containing pharmaceutical compositions and dosage forms disclosed herein contain little or no compound(s) capable of isomerizing the double bond of DMF.

In another aspect, the DMF-containing pharmaceutical compositions and dosage forms disclosed herein contain antioxidants and/or free radical scavengers.

In a sixth aspect, a dosage form for treating multiple sclerosis is provided which comprises (a) dimethyl fumarate in solid form; and (b) one or more compounds of Formula (VI):

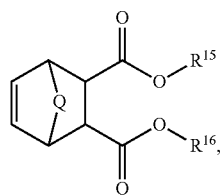

(VI)

isomers thereof, and salts of any of the foregoing, wherein:
Q is —O—, —S—, —NH—, —N(R[17])— or C(R[18])$_2$;
each of R[15] and R[16] is independently chosen from hydrogen and methyl;
R[17] is alkyl; and
each R[18] is independently hydrogen or alkyl; and
(c) a pharmaceutically acceptable vehicle.

In some embodiments, the dimethyl fumarate is in crystalline form. In some embodiments, the dimethyl fumarate is in amorphous form.

In some embodiments, the one or more compounds of Formula (VI) are present in a total combined amount of less than 2 wt % based on the total weight of the dimethyl fumarate.

In some embodiments, the one or more compounds of Formula (VI) are present in a total combined amount of less than 1 wt % based on the total weight of the dimethyl fumarate.

In some embodiments, the one or more compounds of Formula (VI) are present in a combined total amount of less than about 2% by weight based on the total weight of the dimethyl fumarate. In some embodiments, the one or more compounds of Formula (VI) are present in a combined total amount of less than about 1.8% by weight based on the total weight of the dimethyl fumarate. In some embodiments, the one or more compounds of Formula (VI) are present in a combined total amount of less than about 1.6% by weight based on the total weight of the dimethyl fumarate. In some embodiments, the one or more compounds of Formula (VI) are present in a combined total amount of less than about 1.4% by weight based on the total weight of the dimethyl fumarate. In some embodiments, the one or more compounds of Formula (VI) are present in a combined total amount of less than about 1.2% by weight based on the total weight of the dimethyl fumarate. In some embodiments, the one or more compounds of Formula (VI) are present in a combined total amount of less than about 1.0% by weight based on the total weight of the dimethyl fumarate. In some embodiments, the one or more compounds of Formula (VI) are present in a combined total amount of less than about 0.8% by weight based on the total weight of the dimethyl fumarate. In some embodiments, the one or more compounds of Formula (VI) are present in a combined total amount of less than about 0.6% by weight based on the total weight of the dimethyl fumarate. In some embodiments, the one or more compounds of Formula (VI) are present in a combined total amount of less than about 0.4% by weight based on the total weight of the dimethyl fumarate. In some embodiments, the one or more compounds of Formula (VI) are present in a combined total amount of less than about 0.2% by weight based on the total weight of the dimethyl fumarate. In some embodiments, the one or more compounds of Formula (VI) are present in a combined total amount of less than about 0.1% by weight based on the total weight of the dimethyl fumarate.

In some embodiments, the one or more compounds of Formula (VI) are present in a combined total amount of about 0.001% to 2% by weight based on the total weight of the dimethyl fumarate. In some embodiments, the one or more compounds of Formula (VI) are present in a combined total amount of about 0.001% to 1.8% by weight based on the total weight of the dimethyl fumarate. In some embodiments, the one or more compounds of Formula (VI) are present in a combined total amount of about 0.001% to 1.6% by weight based on the total weight of the dimethyl fumarate. In some embodiments, the one or more compounds of Formula (VI) are present in a combined total amount of about 0.001% to 1.4% by weight based on the total weight of the dimethyl fumarate. In some embodiments, the one or more compounds of Formula (VI) are present in a combined total amount of about 0.001% to 1.2% by weight based on the total weight of the dimethyl fumarate. In some embodiments, the one or more compounds of Formula (VI) are present in a combined total amount of about 0.001% to 1.0% by weight based on the total weight of the dimethyl fumarate. In some embodiments, the one or more compounds of Formula (VI) are present in a combined total amount of about 0.001% to 0.8% by weight based on the total weight of the dimethyl fumarate. In some embodiments, the one or more compounds of Formula (VI) are present in a combined total amount of about 0.001% to 0.6% by weight based on the total weight of the dimethyl fumarate. In some embodiments, the one or more compounds of Formula (VI) are present in a combined total amount of about 0.001% to 0.4% by weight based on the total weight of the dimethyl fumarate. In some embodiments, the one or more compounds of Formula (VI) are present in a combined total amount of about 0.001% to 0.2% by weight based on the total weight of the dimethyl fumarate. In some embodiments, the one or more compounds of Formula (VI) are present in a combined total amount of about 0.001% to 0.1% by weight based on the total weight of the dimethyl fumarate.

Compounds of Formula (VI) include the following: the (2,2,1)bicyclo compound in which Q is —O—, and both $R^{15}$ and $R^{16}$ are methyl; the (2,2,1)bicyclo compound in which Q is —O—, $R^{15}$ is H, and $R^{16}$ is methyl; the (2,2,1)bicyclo compound in which Q is —O—, and both $R^{15}$ and $R^{16}$ are H; the (2,2,1)bicyclo compound in which Q is —S—, and both $R^{15}$ and $R^{16}$ are methyl; the (2,2,1)bicyclo compound in which Q is —S—, $R^{15}$ is H, and $R^{16}$ is methyl; the (2,2,1) bicyclo compound in which Q is —S—, and both $R^{15}$ and $R^{16}$ are H; the (2,2,1)bicyclo compound in which Q is —NH—, and both $R^{15}$ and $R^{16}$ are methyl; the (2,2,1) bicyclo compound in which Q is —NH—, $R^{15}$ is H, and $R^{16}$ is methyl; the (2,2,1)bicyclo compound in which Q is —NH—, and both $R^{15}$ and $R^{16}$ are H; the (2,2,1)bicyclo compound in which Q is —NMe-, and both $R^{15}$ and $R^{16}$ are methyl; the (2,2,1)bicyclo compound in which Q is —NMe-, $R^{15}$ is H, and $R^{16}$ is methyl; the (2,2,1)bicyclo compound in which Q is —NMe-, and both $R^{15}$ and $R^{16}$ are H; the (2,2,1)bicyclo compound in which Q is —$CH_2$—, and both $R^{15}$ and $R^{16}$ are methyl; the (2,2,1)bicyclo compound in which Q is —$CH_2$—, $R^{15}$ is H, and $R^{16}$ is methyl; the (2,2,1)bicyclo compound in which Q is —$CH_2$—, and both $R^{15}$ and $R^{16}$ are H; and isomers thereof, and salts of any of the foregoing.

In some embodiments, each of the one or more compounds of Formula (VI) is present in an amount of less than about 0.3% by weight based on the total weight of the dimethyl fumarate. In some embodiments, each of the one or more compounds of Formula (VI) is present in an amount of less than about 0.2% by weight based on the total weight of the dimethyl fumarate. In some embodiments, each of the one or more compounds of Formula (VI) is present in an amount of less than about 0.15% by weight based on the total weight of the dimethyl fumarate. In some embodiments, each of the one or more compounds of Formula (VI) is present in an amount of less than about 0.1% by weight based on the total weight of the dimethyl fumarate. In some embodiments, each of the one or more compounds of Formula (VI) is present in an amount of less than about 0.05% by weight based on the total weight of the dimethyl fumarate.

In some embodiments, each of the one or more compounds of Formula (VI) is present in an amount of about 0.001% to 0.3% by weight based on the total weight of the dimethyl fumarate. In some embodiments, each of the one or more compounds of Formula (VI) is present in an amount of about 0.001% to 0.2% by weight based on the total weight of the dimethyl fumarate. In some embodiments, each of the one or more compounds of Formula (VI) is present in an amount of about 0.001% to 0.15% by weight based on the total weight of the dimethyl fumarate. In some embodiments, each of the one or more compounds of Formula (VI) is present in an amount of about 0.001% to 0.1% by weight based on the total weight of the dimethyl fumarate. In some embodiments, each of the one or more compounds of Formula (VI) is present in an amount of about 0.001% to 0.05% by weight based on the total weight of the dimethyl fumarate.

In another aspect, the DMF-containing pharmaceutical compositions and dosage forms disclosed herein contain little or no compound(s) capable of reacting with DMF to form Diels-Alder products.

For example, DMF, which can act as dienophile, will react with cyclopentadiene, furan, thiofurans, or pyrroles, to form Diels-Alder cyclization products as shown below, where Q, $R^{15}$ and $R^{16}$ are as defined herein:

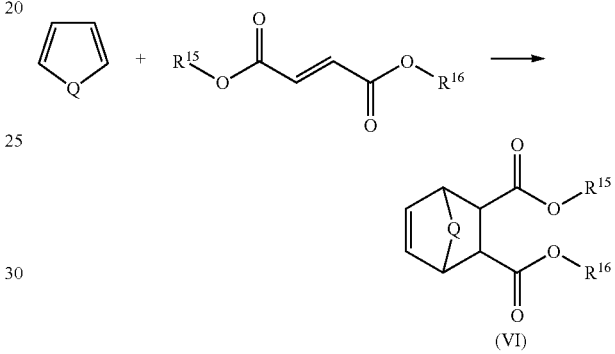

Thus in some embodiments, the pharmaceutical compositions and dosage forms disclosed herein are substantially free of any compounds containing furan, thiophene, and pyrrole moieties.

Pharmaceutical Compositions

Pharmaceutical compositions provided by the present disclosure may comprise a therapeutically effective amount of DMF together with a suitable amount of one or more pharmaceutically acceptable vehicles so as to provide a composition for proper administration to a patient. Suitable pharmaceutical vehicles are described in the art.

In certain embodiments, DMF may be incorporated into pharmaceutical compositions to be administered orally. Oral administration of such pharmaceutical compositions may result in uptake of DMF throughout the intestine and entry into the systemic circulation. Such oral compositions may be prepared in a manner known in the pharmaceutical art and comprise DMF and at least one pharmaceutically acceptable vehicle. Oral pharmaceutical compositions may include a therapeutically effective amount of DMF and a suitable amount of a pharmaceutically acceptable vehicle, so as to provide an appropriate form for administration to a patient.

DMF may be incorporated into pharmaceutical compositions to be administered by any other appropriate route of systemic administration including intramuscular, intravenous and oral.

Pharmaceutical compositions comprising DMF may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of the compound or crystalline forms thereof and one or more pharmaceutically acceptable vehicles into formulations that can be used pharmaceutically. Proper formulation is dependent upon the route of administration chosen. Pharmaceutical compositions provided by the present disclosure take the form of sustained-release formulations suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of DMF calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some applications, maintaining a constant blood and tissue concentration throughout the course of therapy is the most desirable mode of treatment. Immediate release of drug may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodible matrix systems, pH independent formulations, gastric retention systems, and the like.

An appropriate oral dosage form for a particular pharmaceutical composition provided by the present disclosure may depend, at least in part, on the gastrointestinal absorption properties of DMF and/or the stability of DMF in the gastrointestinal tract, the pharmacokinetics of DMF and the intended therapeutic profile. An appropriate controlled release oral dosage form may be selected for a particular compound. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of DMF upon oral administration. Sustained release oral dosage forms may be used to release drugs over a prolonged time period and are useful when it is desired that a drug or drug form be delivered to the lower gastrointestinal tract, including the colon. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

In certain embodiments, pharmaceutical compositions provided by the present disclosure may include any enteric-coated sustained release oral dosage form for administering DMF. In some embodiments, the enteric-coated oral dosage form is administered to a patient at a dosing frequency of three times per day. In some embodiments, the enteric-coated oral dosage form is administered to a patient at a dosing frequency of twice per day. In some embodiments, the enteric-coated oral dosage form is administered to a patient at a dosing frequency of once per day.

In certain embodiments, pharmaceutical compositions provided by the present disclosure may include any suitable dosage forms that achieve the above described in vitro release profiles. Such dosage forms may be any systemic dosage forms, including sustained release enteric-coated oral dosage forms and sustained release enteric-coated or non-enteric-coated oral dosage forms. Examples of suitable dosage forms are described herein. Those skilled in the formulation art can develop any number of acceptable dosage forms given the dosage forms described in the examples as a starting point.

An appropriate dose of DMF may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

The methods and compositions disclosed herein can be used to treat patients suffering from diseases, disorders, conditions, and symptoms for which DMF, MMF (the active metabolite of DMF), and/or other fumaric acid esters are known to provide, or are later found to provide, therapeutic benefit. DMF can be used to treat a disease chosen from adrenal leukodystrophy, AGE-induced genome damage, Alexander Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, paraneoplastic syndromes, Parkinson's disease, Pelizaeus-Merzbacher disease, primary lateral sclerosis, progressive supranuclear palsy, psoriasis, reperfusion injury, retinopathia pigmentosa, Schilder's Disease, subacute necrotizing myelopathy, Susac's syndrome, transplantation rejection, transverse myelitis, a tumor, ulcerative colitis and Zellweger's syndrome.

Methods of treating a disease in a patient provided by the present disclosure comprise administering to a patient in need of such treatment a therapeutically effective amount of DMF. These methods and pharmaceutical compositions provide therapeutic or prophylactic plasma and/or blood concentrations of DMF following administration to a patient. DMF may be administered in an amount and using a dosing schedule as appropriate for treatment of a particular disease. Daily doses of DMF may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, DMF may be administered at a dose over time from about 1 mg to about 5 g per day, from about 10 mg to about 4 g per day, in certain embodiments from about 20 mg to about 2 g per day, in certain embodiments from about 100 mg to about 1 g per day, in certain embodiments from about 200 mg to about 800 mg per day, in certain embodiments from about 300 mg to about 600 mg per day, and in certain embodiments from about 400 mg to about 500 mg per day. An appropriate dose of DMF may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

DMF and/or MMF may be assayed in vitro and in vivo for the desired therapeutic or prophylactic activity prior to use in humans. In vivo assays, for example using appropriate animal models, may also be used to determine whether administration of DMF is therapeutically effective.

In certain embodiments, a therapeutically effective dose of DMF may provide therapeutic benefit without causing substantial toxicity including adverse side effects. Toxicity of DMF and/or metabolites thereof may be determined as described herein and/or by using standard pharmaceutical procedures and may be ascertained by those skilled in the art. The dose ratio between toxic and therapeutic effect is the therapeutic index. A dose of DMF may be within a range capable of establishing and maintaining a therapeutically effective circulating plasma and/or blood concentration of DMF that exhibits little or no toxicity.

DMF administration may be used to treat a disease chosen from adrenal leukodystrophy, AGE-induced genome damage, Alexanders Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, paraneoplastic syndromes, Parkinson's disease, Pelizaeus-Merzbacher disease, primary lateral sclerosis, progressive supranuclear palsy, psoriasis, reperfusion injury, retinopathia pigmentosa, Schilder's Disease, subacute necrotizing myelopathy, Susac's syndrome, transplantation rejection, transverse myelitis, a tumor, ulcerative colitis and Zellweger's syndrome. The underlying etiology of any of the foregoing diseases being treated may have a multiplicity of origins. Further, in certain embodiments, a therapeutically effective amount of DMF may be administered to a patient, such as a human, as a preventative measure against the foregoing diseases and disorders. Thus, a therapeutically effective amount of DMF may be administered as a preventative measure to a patient having a predisposition for and/or history of adrenal leukodystrophy, AGE-induced genome damage, Alexander Disease, Alper's Disease, Alzheimer's disease, amyotrophic lateral sclerosis, angina pectoris, arthritis, asthma, balo concentric sclerosis, Canavan disease, cardiac insufficiency including left ventricular insufficiency, central nervous system vasculitis, Charcott-Marie-Tooth Disease, childhood ataxia with central nervous system hypomyelination, chronic idiopathic peripheral neuropathy, chronic obstructive pulmonary disease, Crohn's disease, diabetic retinopathy, graft versus host disease, hepatitis C viral infection, herpes simplex viral infection, human immunodeficiency viral infection, Huntington's disease, irritable bowel disorder, ischemia, Krabbe Disease, lichen planus, macular degeneration, mitochondrial encephalomyopathy, monomelic amyotrophy, multiple sclerosis, myocardial infarction, neurodegeneration with brain iron accumulation, neuromyelitis optica, neurosarcoidosis, NF-κB mediated diseases, optic neuritis, paraneoplastic syndromes, Parkinson's disease, Pelizaeus-Merzbacher disease, primary lateral sclerosis, progressive supranuclear palsy, psoriasis, reperfusion injury, retinopathia pigmentosa, Schilder's Disease, subacute necrotizing myelopathy, Susac's syndrome, transplantation rejection, transverse myelitis, a tumor, ulcerative colitis and/or Zellweger's syndrome.

Administration

DMF and pharmaceutical compositions thereof may be administered orally or by any other appropriate route suitable for systemic or local administration. For example, systemic administration can be by infusion or bolus injection, by absorption through epithelial or mucocutaneous linings (e.g., oral mucosa, rectal, and intestinal mucosa, etc.). Other suitable routes of systemic administration include, but are not limited to, intradermal, intramuscular, intraperitoneal, intravenous, subcutaneous, intranasal, epidural, oral, sublingual and inhalation. Local administration can be topical (e.g., by applying a DMF-containing cream or lotion to an effected area of skin), or by localized injection into an effected organ (e.g., the eyeball).

The amount of DMF that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of DMF to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of DMF contained within each dosage form may be the same or different. The amount of DMF contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, DMF may exhibit a high therapeutic index. The data obtained from these cell culture assays and animal studies may be used in formulating a dosage range that is not toxic for use in humans. A dose of DMF provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to DMF. Such compounds may be provided to treat the same disease or a different disease than the disease being treated with the DMF.

In certain embodiments, DMF may be used in combination with MMF.

In certain embodiments, DMF may be used in combination with at least one other therapeutic agent. In certain embodiments, DMF may be administered to a patient together with another compound for treating diseases and conditions including: adrenal leukodystrophy, Alexander Disease, Alper's Disease, balo concentric sclerosis, Canavan disease, central nervous system vasculitis, Charcott-Marie-Tooth Disease, childhood ataxia with central nervous system hypomyelination, diabetic retinopathy, graft versus host disease, hepatitis C viral infection, herpes simplex viral infection, human immunodeficiency viral infection, Krabbe Disease, lichen planus, macular degeneration, monomelic amyotrophy, neurodegeneration with brain iron accumulation, neuromyelitis optica, neurosarcoidosis, optic neuritis, paraneoplastic syndromes, Pelizaeus-Merzbacher disease, primary lateral sclerosis, progressive supranuclear palsy, Schilder's Disease, subacute necrotizing myelopathy, Susac's syndrome, transverse myelitis, a tumor and Zellweger's syndrome.

DMF and the at least one other therapeutic agent may act additively or, and in certain embodiments, synergistically. The at least one additional therapeutic agent may be included in the same dosage form as DMF or may be provided in a separate dosage form. Methods provided by the present disclosure can further include, in addition to administering DMF, administering one or more therapeutic agents effective for treating the same or different disease than the disease being treated by DMF. Methods provided by the present disclosure include administration of DMF and one or more other therapeutic agents provided that the combined administration does not inhibit the therapeutic efficacy of the DMF and/or does not typically produce significant and/or substantial adverse combination effects.

In certain embodiments, dosage forms comprising DMF may be administered concurrently with the administration of another therapeutic agent, which may be part of the same dosage form as, or in a different dosage form than that comprising DMF. DMF may be administered prior or subsequent to administration of another therapeutic agent. In certain embodiments, the combination therapy may comprise alternating between administering DMF and a composition comprising another therapeutic agent, e.g., to minimize adverse drug effects associated with a particular drug. When DMF is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising DMF may be administered with one or more substances to enhance, modulate and/or control release, bioavailability, therapeutic efficacy, therapeutic potency, stability, and the like of DMF. For example, to enhance the therapeutic efficacy of DMF, the DMF may be co-administered with or a dosage form comprising DMF and one or more active agents to increase the absorption or diffusion of DMF from the gastrointestinal tract to the systemic circulation, or to inhibit degradation of the DMF in the blood of a patient. In certain embodiments, DMF may be co-administered with an active agent having pharmacological effects that enhance the therapeutic efficacy of DMF.

EXAMPLES

The following examples illustrate various aspects of the disclosure. It will be apparent to those skilled in the art that many modifications, both to materials and methods, may be practiced without departing from the scope of the disclosure.

Example 1: Photodegradation of DMF Under Fluorescent Light

Approximately 100 mg DMF powder (TCI America, Portland, Oreg.) was spread into a thin layer (~1 mm) in open quartz containers. The samples were then placed in an ICH2 Photoreactor (Luzchem Research Inc.) with 16 cool white fluorescent lamps (F8T5/CW—8 Watt) installed. The light power was $21 \times 10^3$ lux with low level of near UV light (320-400 nm) at 2.0 watt/m². Samples were taken out at 0.5, 1, 2 and 24 hours. Solutions of the sample were prepared at 10 mg/mL in diluent (water/acetonitrile/$H_3PO_4$ (80/20/0.05 by volume)), sonicated for 10 minutes, and centrifuged for 10 minutes to remove the insoluble materials. The amount (weight percent) of compound (1) in the samples was determined by reverse phase HPLC using a C18 column and a 30-minute gradient method according to Table 1 where Mobile Phase A is water/0.05% $H_3PO_4$ and Mobile Phase B is water/acetonitrile/$H_3PO_4$ (10/90/0.05 by volume) with UV detection at 210 nm. The rate of formation of compound (1) is shown in FIG. 1 for the first 2 hours, and in FIG. 2 for the full 24 hours.

FIG. 1 shows that about 0.2 wt % of compound (1) is formed using $17.7 \times 10^3$ lux·hr of fluorescent light and about 0.1 wt % of compound (1) is formed using $8.8 \times 10^3$ lux·hr of fluorescent light.

TABLE 1

Gradient for HPLC Method

| Time (minutes) | % Mobile Phase A | % Mobile Phase B |
|---|---|---|
| 0 | 98 | 2 |
| 6 | 65 | 35 |
| 15 | 55 | 45 |
| 25 | 10 | 90 |
| 25.1 | 98 | 2 |
| 30 | 98 | 2 |

Example 2: Photodegradation of DMF Under Near-UV Light

Approximately 100 mg DMF powder (TCI America, Portland, Oreg.) was spread into a thin layer in open quartz containers. The samples were then placed in an ICH2 Photoreactor (Luzchem Research Inc.) with 16 near UV fluorescent lamps (Hitachi FL8BL-B) installed. The near-UV light (320-400 nm) power was 79 watt/$m^2$. Samples were taken out at 10, 20, and 40 minutes. The samples were prepared and analyzed the same way as described in Example 1. The rate of formation of compound (1) is shown in FIG. 3.

Figure 3:
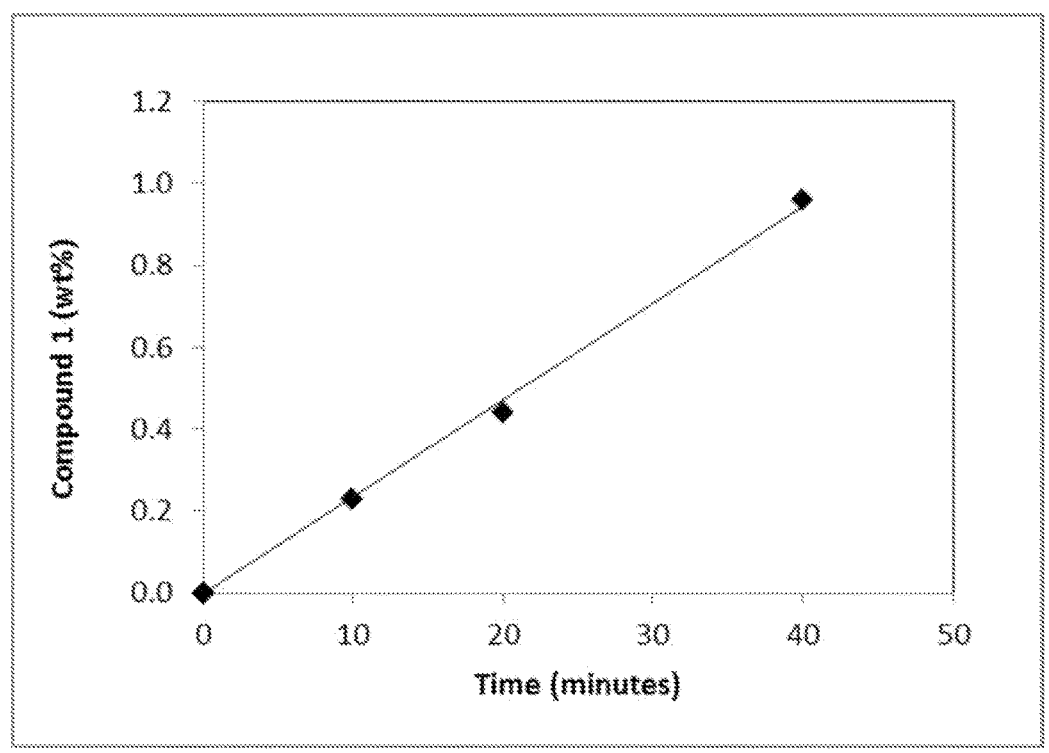
FIG. 3 shows the formation of compound (1) after DMF powder has been exposed to near-UV light.

FIG. 3 shows that about 0.2 wt % of compound (1) is formed using 11.2 watt·hr/$m^2$ of near-UV light, and about 0.1 wt % of compound (1) is formed using 5.6 watt·hr/$m^2$ of near-UV light.

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

The invention claimed is:

1. A dosage form for treating multiple sclerosis, comprising:
   (a) a therapeutically effective amount of dimethyl fumarate in solid form, wherein said dimethyl fumarate is the only drug in the dosage form; and
   (b) one or more compounds of Formula (I):

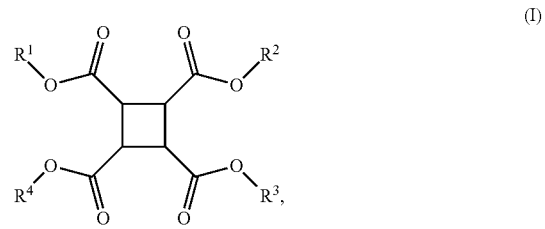

isomers thereof and salts of any of the foregoing, wherein:
each of $R^1$ through $R^4$ is independently chosen from hydrogen and methyl wherein at least one of $R^1$-$R^4$ is hydrogen; and wherein the one or more compounds of Formula (I) are impurities and are present in the dosage form in a combined total amount of 0.001% to 2% by weight based on total weight of the dimethyl fumarate; and
   (c) a pharmaceutically acceptable vehicle.

2. The dosage form of claim 1, wherein the one or more compounds of Formula (I) are present in a combined total amount of 0.001% to less than 1% by weight based on total weight of the dimethyl fumarate.

3. The dosage form of claim 1, wherein the one or more compounds of Formula (I) are selected from 3,4-bis(methoxycarbonyl)cyclobutane-1,2-dicarboxylic acid, 2,4-bis(methoxycarbonyl)cyclobutane-1,3-dicarboxylic acid, cyclobutane-1,2,3,4-tetracarboxylic acid, and isomers thereof and salts of any of the foregoing.

4. The dosage form of claim 1, wherein the one or more compounds of Formula I are 1R, 2R, 3S, 4S-isomers.

5. The dosage form of claim 3, wherein each of the one or more compounds of Formula (I) is in an amount of 0.001% to 0.3% by weight based on total weight of the dimethyl fumarate.

6. The dosage form of claim 3, wherein each of the one or more compounds of Formula (I) is in an amount of 0.001% to 0.2% by weight based on total weight of the dimethyl fumarate.

7. The dosage form of claim 1, wherein the pharmaceutically acceptable vehicle is selected from a carrier, a diluent, an excipient, a wetting agent, an emulsifier, a buffer, a stabilizer, a thickener, a lubricant, a coloring agent and combinations thereof.

8. The dosage form of claim 1, wherein the opaque coating is free of dimethyl fumarate.

9. The dosage form of claim 1, wherein the dosage form is enclosed in a package that limits exposure of the dosage form to ambient light.

10. The dosage form of claim 9, wherein the package is a bottle comprising an opaque polymer.

11. The dosage form of claim 9, wherein the package is a blister pack comprising metal foil.

12. The dosage form of claim 11, wherein the blister pack comprises an opaque polymer.

13. The dosage form of claim 1 wherein the dosage form is in the form of a tablet or capsule having an opaque coating comprising a compound selected from the group consisting of iron oxide, a colorant, titanium dioxide, zinc oxide and combinations thereof and the dosage form does not contain polyvinylpyrrolidine.

* * * * *